(12) United States Patent
Komp et al.

(10) Patent No.: US 11,801,113 B2
(45) Date of Patent: Oct. 31, 2023

(54) THORACIC IMAGING, DISTANCE MEASURING, AND NOTIFICATION SYSTEM AND METHOD

(71) Applicant: COVIDIEN LP, Mansfield, MA (US)

(72) Inventors: John W. Komp, Dillon, CO (US); Irena Cantrall, Boulder, CO (US)

(73) Assignee: COVIDIEN LP, Mansfield, MA (US)

(\*) Notice: Subject to any disclaimer, the term of this patent is extended or adjusted under 35 U.S.C. 154(b) by 656 days.

(21) Appl. No.: 16/682,351

(22) Filed: Nov. 13, 2019

(65) Prior Publication Data

US 2020/0188032 A1 Jun. 18, 2020

Related U.S. Application Data

(60) Provisional application No. 62/782,683, filed on Dec. 20, 2018, provisional application No. 62/779,242, (Continued)

(51) Int. Cl.
*A61B 90/00* (2016.01)
*A61B 1/00* (2006.01)
(Continued)

(52) U.S. Cl.
CPC .......... *A61B 90/36* (2016.02); *A61B 1/00004* (2013.01); *A61B 1/00042* (2022.02); (Continued)

(58) Field of Classification Search
CPC . A61B 34/20; A61B 1/00004; A61B 1/00045; A61B 1/04; A61B 2034/2065; (Continued)

(56) References Cited

U.S. PATENT DOCUMENTS 3,928,925 A \* 12/1975 Gay, Jr. ................. G09B 29/12
434/152
5,057,494 A 10/1991 Sheffield
(Continued)

FOREIGN PATENT DOCUMENTS

BR 0013237 A 7/2003
BR 0116004 A 6/2004
(Continued)

OTHER PUBLICATIONS

European Search Report issued in European Patent Application No. EP 19215517 dated Apr. 14, 2020, 9 pages.
(Continued)

*Primary Examiner* — Anh Tuan T Nguyen
*Assistant Examiner* — Shankar Raj Ghimire
(74) *Attorney, Agent, or Firm* — WEBER ROSSELLI & CANNON LLP

(57) ABSTRACT

A system and method for enhanced surgical navigation and graphical user interfaces associated therewith. The system includes a 3D endoscope and a computing device including a display for displaying the graphical user interfaces. The 3D endoscope includes a camera source and a scan source and is utilized to generate a 3D spatial map of a surgical site. A position of a surgical tool is detected in the 3D spatial map, a distance between the position of the surgical tool in the 3D spatial map and a location of an anatomy is detected, and a warning is generated when it is determined that the distance between the position of the surgical tool in the 3D spatial map and the location of the anatomy is equal to or not greater than a threshold minimum distance.

20 Claims, 10 Drawing Sheets

Related U.S. Application Data filed on Dec. 13, 2018, provisional application No. 62/779,229, filed on Dec. 13, 2018.

(51) Int. Cl.
*A61B 34/20* (2016.01)
*G06T 7/50* (2017.01)
*G06T 7/70* (2017.01)
*G06F 9/54* (2006.01)
*A61B 1/06* (2006.01)

(52) U.S. Cl.
CPC .... *A61B 1/00045* (2013.01); *A61B 1/000094* (2022.02); *A61B 1/00097* (2022.02); *A61B 1/00194* (2022.02); *A61B 1/0605* (2022.02); *A61B 34/20* (2016.02); *G06F 9/542* (2013.01); *G06T 7/50* (2017.01); *G06T 7/70* (2017.01); *A61B 2034/2065* (2016.02); *G06T 2207/10068* (2013.01)

(58) Field of Classification Search
CPC ............ A61B 2090/367; A61B 5/1076; A61B 2090/365; G06T 7/70; G06T 2207/10068; G01S 7/52073
See application file for complete search history.

(56) References Cited

U.S. PATENT DOCUMENTS

| | | |
|---|---|---|
| 5,321,113 A | 6/1994 | Cooper et al. |
| 5,687,737 A | 11/1997 | Branham et al. |
| 6,003,517 A | 12/1999 | Sheffield et al. |
| 7,474,407 B2 | 1/2009 | Gutin |
| 7,538,859 B2 | 5/2009 | Tearney et al. |
| 7,559,895 B2 | 7/2009 | Stetten et al. |
| 7,756,305 B2 | 7/2010 | Price |
| 7,857,756 B2 | 12/2010 | Warren et al. |
| 7,949,385 B2 | 5/2011 | Khamene et al. |
| 7,952,718 B2 | 5/2011 | Li et al. |
| 8,335,359 B2 | 12/2012 | Fidrich et al. |
| 8,335,557 B2 | 12/2012 | Maschke |
| 8,382,662 B2 | 2/2013 | Soper et al. |
| 8,384,909 B2 | 2/2013 | Yun et al. |
| 8,460,195 B2 | 6/2013 | Courtney et al. |
| 8,494,794 B2 | 7/2013 | Dutta et al. |
| 8,706,184 B2 | 4/2014 | Mohr et al. |
| 8,784,321 B2 | 7/2014 | Courtney et al. |
| 8,827,934 B2 | 9/2014 | Chopra et al. |
| 8,983,580 B2 | 3/2015 | Boppart et al. |
| 9,375,268 B2 | 6/2016 | Long |
| 9,398,936 B2 | 7/2016 | Razzaque et al. |
| 9,554,774 B2 | 1/2017 | Moore et al. |
| 9,861,338 B2 | 1/2018 | Kanade et al. |
| 9,918,659 B2 | 3/2018 | Chopra et al. |
| 10,004,558 B2 | 6/2018 | Long |
| 10,194,897 B2 | 2/2019 | Cedro et al. |
| 10,350,009 B2* | 7/2019 | Panescu ............... A61B 1/0004 |
| 10,368,054 B2* | 7/2019 | Panescu ................. H04N 13/25 |
| 10,373,719 B2 | 8/2019 | Soper et al. |
| 10,376,178 B2 | 8/2019 | Chopra |
| 10,391,277 B2 | 8/2019 | Rahimian et al. |
| 10,405,753 B2 | 9/2019 | Sorger |
| 10,478,162 B2 | 11/2019 | Barbagli et al. |
| 10,480,926 B2 | 11/2019 | Froggatt et al. |
| 10,524,866 B2 | 1/2020 | Srinivasan et al. |
| 10,555,788 B2 | 2/2020 | Panescu et al. |
| 10,569,071 B2 | 2/2020 | Harris et al. |
| 10,603,106 B2 | 3/2020 | Weide et al. |
| 10,610,306 B2 | 4/2020 | Chopra |
| 10,638,953 B2 | 5/2020 | Duindam et al. |
| 10,639,114 B2 | 5/2020 | Schuh et al. |
| 10,674,970 B2 | 6/2020 | Averbuch et al. |
| 10,682,070 B2 | 6/2020 | Duindam |
| 10,702,137 B2 | 7/2020 | Deyanov |
| 10,706,543 B2 | 7/2020 | Donhowe et al. |
| 10,709,506 B2 | 7/2020 | Coste-Maniere et al. |
| 10,772,485 B2 | 9/2020 | Schlesinger et al. |
| 10,796,432 B2 | 10/2020 | Mintz et al. |
| 10,823,627 B2 | 11/2020 | Sanborn et al. |
| 10,827,913 B2 | 11/2020 | Ummalaneni et al. |
| 10,835,153 B2 | 11/2020 | Rafii-Tari et al. |
| 10,885,630 B2 | 1/2021 | Li et al. |
| 11,172,184 B2 | 11/2021 | Komp et al. |
| 2002/0147462 A1 | 10/2002 | Mair et al. |
| 2003/0013972 A1 | 1/2003 | Makin |
| 2003/0164952 A1* | 9/2003 | Deichmann ............ B33Y 50/00 356/603 |
| 2004/0120981 A1 | 6/2004 | Nathan |
| 2004/0210105 A1* | 10/2004 | Hale ................... A61B 1/00183 600/101 |
| 2006/0084860 A1* | 4/2006 | Geiger .................... G06T 15/08 600/407 |
| 2008/0045938 A1 | 2/2008 | Weide et al. |
| 2011/0282188 A1* | 11/2011 | Burnside ............ A61B 17/3403 600/424 |
| 2013/0018255 A1* | 1/2013 | Kitamura ......... A61B 1/000094 600/424 |
| 2013/0303945 A1 | 11/2013 | Blumenkranz et al. |
| 2014/0035798 A1 | 2/2014 | Kawada et al. |
| 2014/0336461 A1* | 11/2014 | Reiter ...................... A61B 1/06 600/111 |
| 2015/0148690 A1 | 5/2015 | Chopra et al. |
| 2015/0235373 A1* | 8/2015 | Kato ................... A61B 1/00194 348/51 |
| 2015/0265368 A1 | 9/2015 | Chopra et al. |
| 2016/0157939 A1 | 6/2016 | Larkin et al. |
| 2016/0183841 A1 | 6/2016 | Duindam et al. |
| 2016/0192860 A1 | 7/2016 | Allenby et al. |
| 2016/0287344 A1 | 10/2016 | Donhowe et al. |
| 2017/0035380 A1* | 2/2017 | Barak .................... A61B 5/743 |
| 2017/0112571 A1 | 4/2017 | Thiel et al. |
| 2017/0112576 A1 | 4/2017 | Coste-Maniere et al. |
| 2017/0172662 A1* | 6/2017 | Panescu ................. A61B 34/20 |
| 2017/0209071 A1* | 7/2017 | Zhao ..................... A61B 5/065 |
| 2017/0265952 A1 | 9/2017 | Donhowe et al. |
| 2017/0311844 A1 | 11/2017 | Zhao et al. |
| 2017/0319165 A1 | 11/2017 | Averbuch |
| 2018/0078318 A1 | 3/2018 | Barbagli et al. |
| 2018/0144092 A1 | 5/2018 | Flitsch et al. |
| 2018/0153621 A1 | 6/2018 | Duindam et al. |
| 2018/0235709 A1 | 8/2018 | Donhowe et al. |
| 2018/0240237 A1 | 8/2018 | Donhowe et al. |
| 2018/0256262 A1 | 9/2018 | Duindam et al. |
| 2018/0263527 A1* | 9/2018 | Kitamura ......... A61B 1/000094 |
| 2018/0263706 A1 | 9/2018 | Averbuch |
| 2018/0279852 A1 | 10/2018 | Rafii-Tari et al. |
| 2018/0310831 A1* | 11/2018 | Cheng .................. A61B 5/6851 |
| 2018/0325419 A1 | 11/2018 | Zhao et al. |
| 2018/0356493 A1* | 12/2018 | Stapert .................. A61B 34/20 |
| 2019/0000559 A1 | 1/2019 | Berman et al. |
| 2019/0000560 A1 | 1/2019 | Berman et al. |
| 2019/0008413 A1 | 1/2019 | Duindam et al. |
| 2019/0038365 A1 | 2/2019 | Soper et al. |
| 2019/0065209 A1 | 2/2019 | Mishra et al. |
| 2019/0110839 A1 | 4/2019 | Rafii-Tari et al. |
| 2019/0175062 A1 | 6/2019 | Rafii-Tari et al. |
| 2019/0175799 A1 | 6/2019 | Hsu et al. |
| 2019/0183318 A1 | 6/2019 | Froggatt et al. |
| 2019/0183585 A1 | 6/2019 | Rafii-Tari et al. |
| 2019/0183587 A1 | 6/2019 | Rafii-Tari et al. |
| 2019/0192234 A1 | 6/2019 | Gadda et al. |
| 2019/0209016 A1 | 7/2019 | Herzlinger et al. |
| 2019/0209043 A1 | 7/2019 | Zhao et al. |
| 2019/0216548 A1 | 7/2019 | Ummalaneni |
| 2019/0239723 A1 | 8/2019 | Duindam et al. |
| 2019/0239831 A1 | 8/2019 | Chopra |
| 2019/0250050 A1 | 8/2019 | Sanborn et al. |
| 2019/0254649 A1 | 8/2019 | Walters et al. |
| 2019/0269470 A1 | 9/2019 | Barbagli et al. |
| 2019/0269818 A1 | 9/2019 | Dhanaraj et al. |
| 2019/0269819 A1 | 9/2019 | Dhanaraj et al. |
| 2019/0272634 A1 | 9/2019 | Li et al. |
| 2019/0298160 A1 | 10/2019 | Ummalaneni et al. |

(56) References Cited

U.S. PATENT DOCUMENTS

| | | |
|---|---|---|
| 2019/0298451 A1 | 10/2019 | Wong et al. |
| 2019/0320878 A1 | 10/2019 | Duindam et al. |
| 2019/0320937 A1 | 10/2019 | Duindam et al. |
| 2019/0336238 A1* | 11/2019 | Yu .................. A61B 1/018 |
| 2019/0343424 A1 | 11/2019 | Blumenkranz et al. |
| 2019/0350659 A1 | 11/2019 | Wang et al. |
| 2019/0365199 A1 | 12/2019 | Zhao et al. |
| 2019/0365479 A1 | 12/2019 | Rafii-Tari |
| 2019/0365486 A1 | 12/2019 | Srinivasan et al. |
| 2019/0380787 A1 | 12/2019 | Ye et al. |
| 2020/0000319 A1 | 1/2020 | Saadat et al. |
| 2020/0000526 A1 | 1/2020 | Zhao |
| 2020/0008655 A1 | 1/2020 | Schlesinger et al. |
| 2020/0020127 A1* | 1/2020 | Hirakawa .......... A61B 1/00009 |
| 2020/0030044 A1 | 1/2020 | Wang et al. |
| 2020/0030461 A1 | 1/2020 | Sorger |
| 2020/0038750 A1 | 2/2020 | Kojima |
| 2020/0043207 A1 | 2/2020 | Lo et al. |
| 2020/0046431 A1 | 2/2020 | Soper et al. |
| 2020/0046436 A1 | 2/2020 | Tzeisler et al. |
| 2020/0054398 A1* | 2/2020 | Kovtun .................. G16H 40/63 |
| 2020/0054399 A1 | 2/2020 | Duindam et al. |
| 2020/0054408 A1 | 2/2020 | Schuh et al. |
| 2020/0060771 A1 | 2/2020 | Lo et al. |
| 2020/0069192 A1 | 3/2020 | Sanborn et al. |
| 2020/0077870 A1 | 3/2020 | Dicarlo et al. |
| 2020/0078023 A1 | 3/2020 | Cedro et al. |
| 2020/0078095 A1 | 3/2020 | Chopra et al. |
| 2020/0078103 A1 | 3/2020 | Duindam et al. |
| 2020/0085514 A1 | 3/2020 | Blumenkranz |
| 2020/0107886 A1* | 4/2020 | Govari .................. A61B 5/066 |
| 2020/0109124 A1 | 4/2020 | Pomper et al. |
| 2020/0129045 A1 | 4/2020 | Prisco |
| 2020/0129239 A1 | 4/2020 | Bianchi et al. |
| 2020/0138514 A1 | 5/2020 | Blumenkranz et al. |
| 2020/0138515 A1 | 5/2020 | Wong |
| 2020/0142013 A1 | 5/2020 | Wong |
| 2020/0155116 A1 | 5/2020 | Donhowe et al. |
| 2020/0155232 A1 | 5/2020 | Wong |
| 2020/0170623 A1 | 6/2020 | Averbuch |
| 2020/0170720 A1 | 6/2020 | Ummalaneni |
| 2020/0179058 A1 | 6/2020 | Barbagli et al. |
| 2020/0188021 A1 | 6/2020 | Wong et al. |
| 2020/0188038 A1 | 6/2020 | Donhowe et al. |
| 2020/0205903 A1 | 7/2020 | Srinivasan et al. |
| 2020/0205904 A1 | 7/2020 | Chopra |
| 2020/0214664 A1 | 7/2020 | Zhao et al. |
| 2020/0229679 A1 | 7/2020 | Zhao et al. |
| 2020/0242767 A1 | 7/2020 | Zhao et al. |
| 2020/0275860 A1 | 9/2020 | Duindam |
| 2020/0297442 A1 | 9/2020 | Adebar et al. |
| 2020/0315554 A1 | 10/2020 | Averbuch et al. |
| 2020/0330795 A1 | 10/2020 | Sawant et al. |
| 2020/0352427 A1 | 11/2020 | Deyanov |
| 2020/0364865 A1 | 11/2020 | Donhowe et al. |
| 2020/0383750 A1 | 12/2020 | Kemp et al. |
| 2021/0000524 A1 | 1/2021 | Barry et al. |
| 2021/0220078 A1* | 7/2021 | Godhani .............. A61B 90/36 |

FOREIGN PATENT DOCUMENTS

| | | |
|---|---|---|
| BR | 0307259 A | 12/2004 |
| BR | 0412298 A2 | 9/2006 |
| BR | 112018003862 A2 | 10/2018 |
| CZ | 1644519 | 12/2008 |
| CZ | 486540 | 9/2016 |
| CZ | 2709512 | 8/2017 |
| CZ | 2884879 | 1/2020 |
| EP | 1644519 B1 | 12/2008 |
| EP | 2141497 A1 | 1/2010 |
| EP | 3225151 A1 | 10/2017 |
| EP | 3413830 A4 | 9/2019 |
| EP | 3478161 A4 | 2/2020 |
| EP | 3641686 A2 | 4/2020 |
| EP | 3644885 A1 | 5/2020 |
| EP | 3644886 A1 | 5/2020 |
| EP | 3749239 A1 | 12/2020 |
| MX | PA03005028 A | 1/2004 |
| MX | PA03000137 A | 9/2004 |
| MX | PA03006874 A | 9/2004 |
| MX | 225663 B | 1/2005 |
| MX | 226292 | 2/2005 |
| MX | PA03010507 A | 7/2005 |
| MX | PA05011725 A | 5/2006 |
| MX | 06011286 | 3/2007 |
| MX | 246862 B | 6/2007 |
| MX | 2007006441 A | 8/2007 |
| MX | 265247 | 3/2009 |
| MX | 284569 B | 3/2011 |

OTHER PUBLICATIONS

Notice of Allowance issued in U.S. Appl. No. 17/521,714 dated Apr. 7, 2023.

* cited by examiner

THORACIC IMAGING, DISTANCE MEASURING, AND NOTIFICATION SYSTEM AND METHOD

CROSS-REFERENCE TO RELATED APPLICATION

This application claims the benefit of U.S. Provisional Application Ser. No. 62/779,229, filed on Dec. 13, 2018, and is related to, and claims the benefit of, U.S. Provisional Application Ser. No. 62/779,242, filed on Dec. 13, 2018 and U.S. Provisional Application Ser. No. 62/782,683, filed on Dec. 20, 2018, the entire contents of each of which being incorporated by reference herein.

BACKGROUND

Technical Field

The disclosure relates to surgical systems, and more particularly, to systems and methods of performing endoscopic thoracic imaging and treatment.

Description of Related Art

Current monocular optical devices (e.g. endoscope, bronchoscope, colonoscope) used for viewing surgical fields during minimally invasive surgery (e.g. laparoscopy) and visual diagnostic procedures (e.g. colonoscopy, bronchoscopy) provide limited reference information on the absolute position of surgical tools and anatomical features because the image has no depth of field. To compensate, surgeons may advance the surgical tool until it comes in contact with a feature or another tool. This leads to inefficient motion and the potential for perforation of critical anatomical structures. Binocular (also known as stereoscopic) optical devices provide limited depth of field affording the surgeon visual information on the distance between items within the optical device's field of view. The accuracy of distance information is limited based on the amount of parallax provided by the optical paths, determined by the distance between the optical paths, and the amount of overlap between the two optical paths.

SUMMARY

The disclosure is directed to derivation and display of distance references between objects both within the current optical view and previously viewed objects that may no longer be in view. This information may be displayed in multiple modalities: point to point distance from a tool to a specific anatomical reference or other tool, point to point distance from a tool to the closest anatomical feature, guard band fencing keep-out regions around critical anatomy, distance to all surfaces in the optical view through usage of a gradient display via color, numerical scale or audio feedback, and user placed scales used started and oriented from a fixed anatomical location (e.g. a ruler starting at the splenic flexure running to the hepatic flexure, a hatch marked arc of defined radius from a fixed point denoting range of lymph node harvesting). The combined distance information and optical endoscope view may be projected on two-dimensional monitors, through augmented reality (AR) displays, or mixed into virtual reality (VR) displays.

In an aspect of the disclosure, a method for enhanced surgical navigation is provided. The method includes generating a 3D spatial map of a surgical site using a scanning 3D endoscope including a camera source and a scan source, receiving a selection of an anatomy in the surgical site, receiving a selection of a threshold minimum distance from the received selection of the anatomy, detecting a position of a surgical tool in the generated 3D spatial map, and measuring a distance between the detected position of the surgical tool in the generated 3D spatial map and the received selection of the anatomy. Additionally, the method includes determining whether the measured distance between the detected position of the surgical tool in the generated 3D spatial map and the received selection of the anatomy is greater than the threshold minimum distance from the received selection of the anatomy, and generating a warning when it is determined that the measured distance between the detected position of the surgical tool in the generated 3D spatial map and the received selection of the anatomy is equal to or not greater than the threshold minimum distance from the received selection of the anatomy. In an aspect, the scan source is an IR scan source.

In an aspect, the method further includes displaying a value representing the measured distance between the detected position of the surgical tool in the generated 3D spatial map and the received selection of the anatomy in a first form when it is determined that the measured distance between the detected position of the surgical tool in the generated 3D spatial map and the received selection of the anatomy is greater than the threshold minimum distance from the received selection of the anatomy, Generating the warning may include displaying the value in a second form different from the first form. Generating the warning may include generating at least one of an audible notification, a tactile notification (e.g., a shake, vibration, or other imposition on the user's hand), or a visual notification.

In an aspect, receiving the selection of the anatomy in the surgical site includes receiving the selection from pre-surgical imagery during a planning phase, the pre-surgical imagery including at least one of CT, MRI, fluoroscopic, ultrasound, or any combinations thereof, Additionally, or alternatively, receiving the selection of the anatomy in the surgical site may include receiving the selection from surgical imagery during a surgical phase from images generated from the 3D endoscope.

Receiving the selection of the threshold minimum distance from the received selection of the anatomy may include receiving the selection from pre-surgical imagery during a planning phase, the pre-surgical imagery including at least one of CT, fluoroscopic, ultrasound, or any combinations thereof. Additionally, or alternatively, receiving the selection of the threshold minimum distance from the received selection of the anatomy includes receiving the selection from surgical imagery during a surgical phase from images generated from the 3D endoscope. Additionally, or alternatively, the selection is a pre-set value based on user (e.g., surgeon) preference or defined by procedure type.

In aspect, the 3D spatial map includes a matrix of equidistant data points representing fixed points in a current view of the surgical site and a value of a data point represents an existence of an object at the data point in space. Additionally, or alternatively, measuring the distance between the detected position of the surgical tool in the generated 3D spatial map and the received selection of the anatomy may include at least one of calculating a difference between coordinates of two data points in the matrix or following a contour of a surface between two data points in the matrix and calculating a distance along the contour.

In another aspect of the disclosure, a system for enhanced surgical navigation is provided including a scanning 3D endoscope including a camera source and a scan source and a computing device operably coupled to the 3D endoscope. The 3D endoscope is configured to be used to generate a 3D spatial map of a surgical site. The computing device is configured to display the 3D spatial map of the surgical site on a graphical user interface, receive a selection of an anatomy in the surgical site, receive a selection of a threshold minimum distance from the received selection of the anatomy, detect a position of a surgical tool in the generated 3D spatial map, and measure a distance between the detected position of the surgical tool in the generated 3D spatial map and the received selection of the anatomy. The computing device further determines whether the measured distance between the detected position of the surgical tool in the generated 3D spatial map and the received selection of the anatomy is greater than the threshold minimum distance from the received selection of the anatomy. Additionally, the computing device generates a warning when it is determined that the measured distance between the detected position of the surgical tool in the generated 3D spatial map and the received selection of the anatomy is equal to or not greater than the threshold minimum distance from the received selection of the anatomy. In an aspect, the scan source is an IR scan source.

In an aspect, the computing device displays, on a graphic user interface, a value representing the measured distance between the detected position of the surgical tool in the generated 3D spatial map and the received selection of the anatomy in a first form when it is determined that the measured distance between the detected position of the surgical tool in the generated 3D spatial map and the received selection of the anatomy is greater than the threshold minimum distance from the received selection of the anatomy, and displays, on a graphic user interface, the value in a second form different from the first form when it is determined that the measured distance between the detected position of the surgical tool in the generated 3D spatial map and the received selection of the anatomy is equal to or not greater than the threshold minimum distance from the received selection of the anatomy.

The generated warning may include at least one of an audible notification, a tactile notification (e.g., a shake, vibration, or other imposition on the user's hand), or a visual notification.

In an aspect, the computing device receives the selection of the anatomy in the surgical site by receiving the selection from pre-surgical imagery during a planning phase, the pre-surgical imagery including at least one of CT, MRI, fluoroscopic, ultrasound, or any combinations thereof. Additionally, or alternatively, the computing device may receive the selection of the anatomy in the surgical site by receiving the selection from surgical imagery during a surgical phase from images generated from the 3D endoscope.

In an aspect, the computing device may receive a selection of the threshold minimum distance from the received selection of the anatomy by receiving the selection from pre-surgical imagery during a planning phase, the pre-surgical imagery including at least one of CT, MRI, fluoroscopic, ultrasound, or any combinations thereof. Additionally, or alternatively, the computing device may receive a selection of the threshold minimum distance from the received selection of the anatomy by receiving the selection from surgical imagery during a surgical phase from images generated from the 3D endoscope. Additionally, or alternatively, the selection is a pre-set value based on user (e.g., surgeon) preference or defined by procedure type.

In an aspect, the 3D spatial map includes a matrix of equidistant data points representing fixed points in a current view of the surgical site and a value of a data point represents an existence of an object at the data point in space. The computing device may measure the distance between the detected position of the surgical tool in the generated 3D spatial map and the received selection of the anatomy by calculating a difference between coordinates of two data points in the matrix or following a contour of a surface between two data points in the matrix and calculating a distance along the contour.

In yet another aspect of the disclosure a non-transitory computer-readable storage medium encoded with a program, that when executed by a processor, causes the processor to generate a 3D spatial map of a surgical site, detect a position of a surgical tool in the generated 3D spatial map, determine whether a distance between the detected position of the surgical tool in the generated 3D spatial map and a location of an anatomy in the 3D spatial map is greater than a threshold minimum distance. A warning is generated when it is determined that the distance between the detected position of the surgical tool in the generated 3D spatial map and the location of the anatomy is equal to or not greater than the threshold minimum distance.

The 3D spatial map may include a matrix of equidistant data points representing fixed points in a current view of the surgical site. Additionally, a value of a data point may represent an existence of an object at the data point in space. The distance between the detected position of the surgical tool in the generated 3D spatial map and the location of the anatomy may be measured by at least one of calculating a difference between coordinates of two data points in the matrix or following a contour of a surface between two data points in the matrix and calculating a distance along the contour.

BRIEF DESCRIPTION OF THE DRAWINGS

Various aspects and features of the disclosure are described hereinbelow with references to the drawings, wherein.

DETAILED DESCRIPTION

Figure 1:
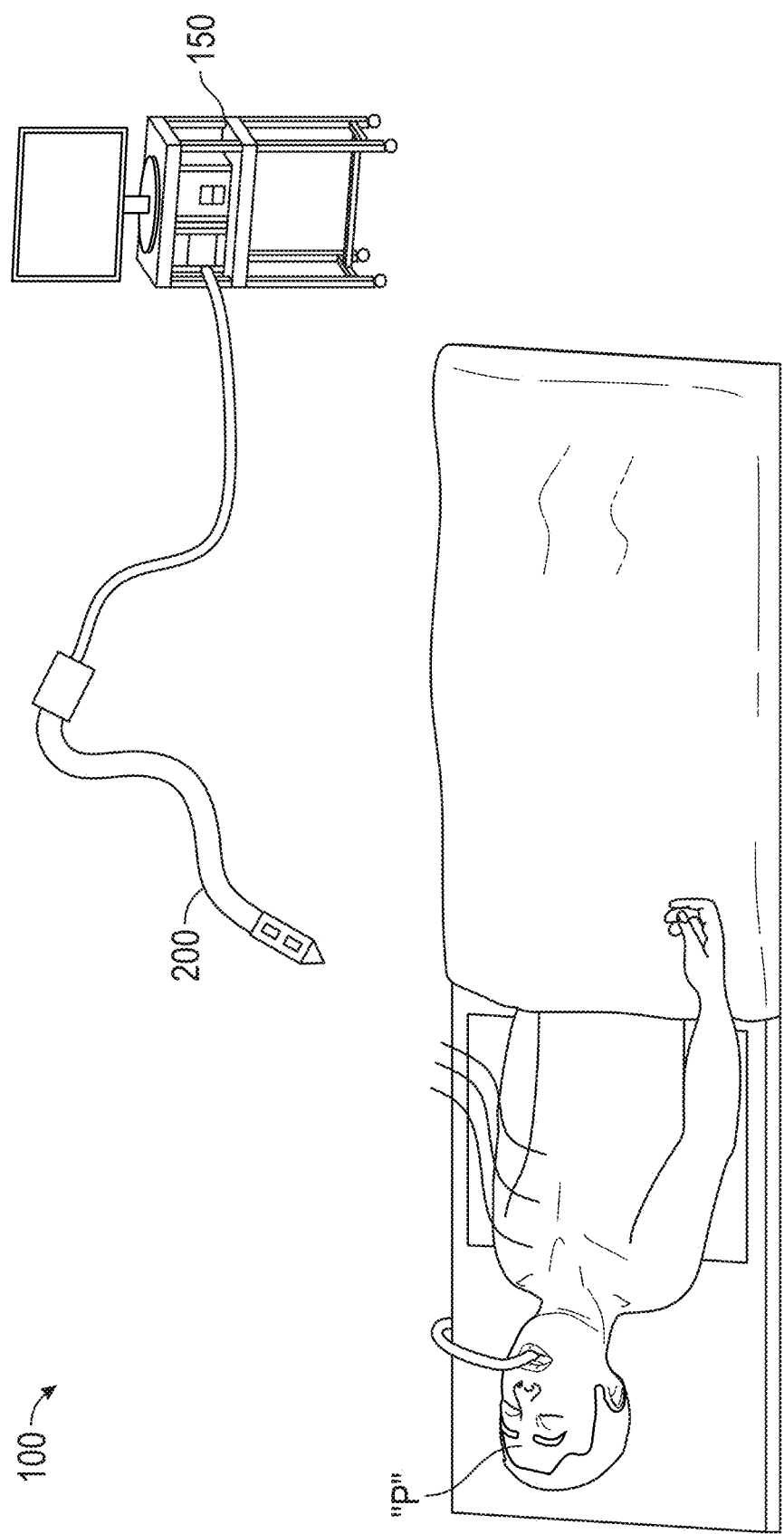
FIG. 1 is a schematic illustration of a surgical imaging system including a 3D endoscope and a computing device for generating, and continually updating in real-time, a 3D spatial map in accordance with the disclosure.

One aspect of the disclosure is directed to a 3D endoscope and systems that support organ matching to preoperative images, for example images of a lung, other anatomy or anatomical features within a surgical site. The 3D endoscope can provide both visual imaging and also surface mapping and is used to generate a 3D spatial map, either by the 3D endoscope or by another component of the system such as a computing device. The computing device utilizes the 3D spatial map to provide enhanced navigational guidance including distance measurements and warnings or other notifications when a surgical device is placed near or is approaching a portion of the anatomy within the surgical site.

In accordance with the disclosure, as will be described in greater detail below, the 3D endoscope (also referred to herein as the "endoscope") includes a structured light (or laser) scanner. As can be appreciated, the structured light scanner may employ infrared light so as to avoid interference from visible light sources, although it is contemplated that the structured light scanner may emit light in the visible spectrum, or any other wavelength, depending upon the tissue being scanned during the procedure. The structured light source includes a known position relative to a camera and permits the calculation of the exact location of the intersection between the light ray from the structured light source and the camera. This information can be scanned as single points, lines, or arrays to create topologic maps of surfaces. In embodiments, the structured light source is that of an LED or LED infrared laser that is dispersed into a scan pattern (line, mesh, or dots), buy rotating mirror, beam splitter, or diffraction grating. In one non-limiting embodiment, the structured light source may be a LED laser having collimated light. The laser scanner will enable visualization systems to achieve accurate surface maps of the lung needed in order to match preoperative computed images to the operative image delivered to the endoscopic camera. Having both in one endoscope offers additional advantage of matching the preoperative computed image to the current camera view as the camera offset is known relative to the surface scan.

In particular applications, the endoscope position will also be tracked by intraoperative instrument tracking systems for example electromagnetic navigation systems. The locational information obtained by the intraoperative instrument tracking system aids in simplifying the algorithms needed to produce large-scale spatial surface maps from segmental sized scans taken from an endoscope. Further, this immediate intraoperative guidance of the optical image location to the surface map and preoperative computed images provides even greater clarity of location and orientation of the endoscope.

In certain embodiments, the 3D endoscope is positionable by a robotic system. The robotic system provides precise six-axis orientation of the endoscope in a similar manner to the navigation systems but benefited by active positioning as well as locational knowledge of the endoscope within the patient. As can be appreciated, the robot may be utilized to autonomously move the endoscope to complete scans of larger areas or whole organs.

In one embodiment, the endoscope includes a visual-light optical camera, a light source of preferably at least one light-emitting diode (LED), a scanning laser, and a second camera used to map the laser. In some embodiments, the scanning laser (and/or visual light) may be detected by the same optical camera in near to mid infrared imaging as optical sensor technology continues to advance. In its simplest form, as detailed below, the endoscope uses a typical arrangement of these components on the distal end of the endoscope. In order to reduce the required distal end diameter of the instrument and to improve triangulation between the laser and the second camera, these four components may have a location on at least one extensible surface. This enables the four components to be arranged along the side of the extensible surface such that the needed space for the individual components is provided by having a cross section equal or slightly larger than any single component and sufficient length to align the components side by side.

The computation of the topology viewed by the endoscope may require a calibration source to detail the alignment of the laser with the second camera. Anticipated is that the calibration may be conducted at the time of manufacture and stored within a memory coupled to a suitable computer, as will be described in detail hereinbelow, or by targeting a calibration surface at the time of use. The calibration will be used internally with the device anticipating the computational topology that may be created with the endoscope and transmitted for clinician via common video transmission means or the raw camera data along with the calibration may be transmitted to an external graphics processor creating the computational topology.

In some embodiments, at least the laser and the second camera may be spaced along the length of the instrument shaft to enable triangulation where the laser and second camera are directed at an angle from the centerline of the instrument.

One advantage of the disclosure is to enable 3D surfacing of organs and other anatomical features and objects in a surgical site, which can be matched to preoperative computational imaging needed for operative guidance to target lesions with particular special knowledge of adjacent structures and anatomic boundaries such as in sublobar resection or lung cancer. Primary use for this system is thoracic but one can vision equal value in deep pelvic, rectal surgery, or other surgical applications. These and further aspects of the disclosure are detailed herein below.

Figure 2:
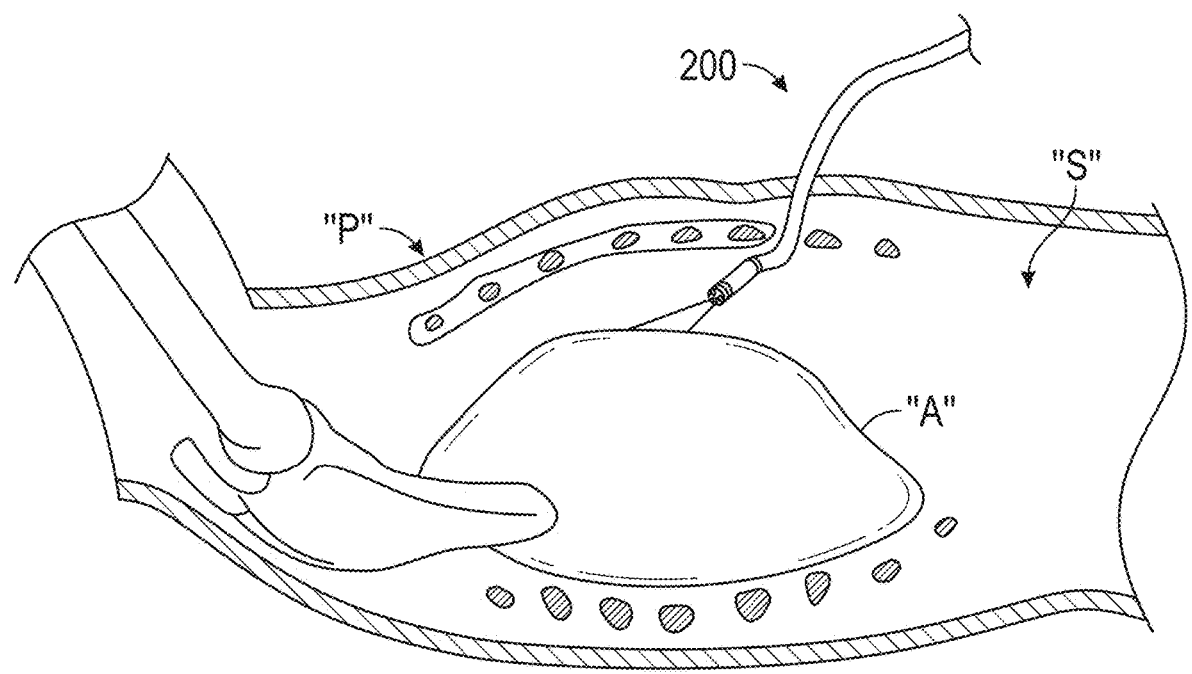
FIG. 2 is a side, cross-sectional, view of the thoracic cavity of a patient with the 3D endoscope of FIG. 1 advanced therein.
Figure 3:
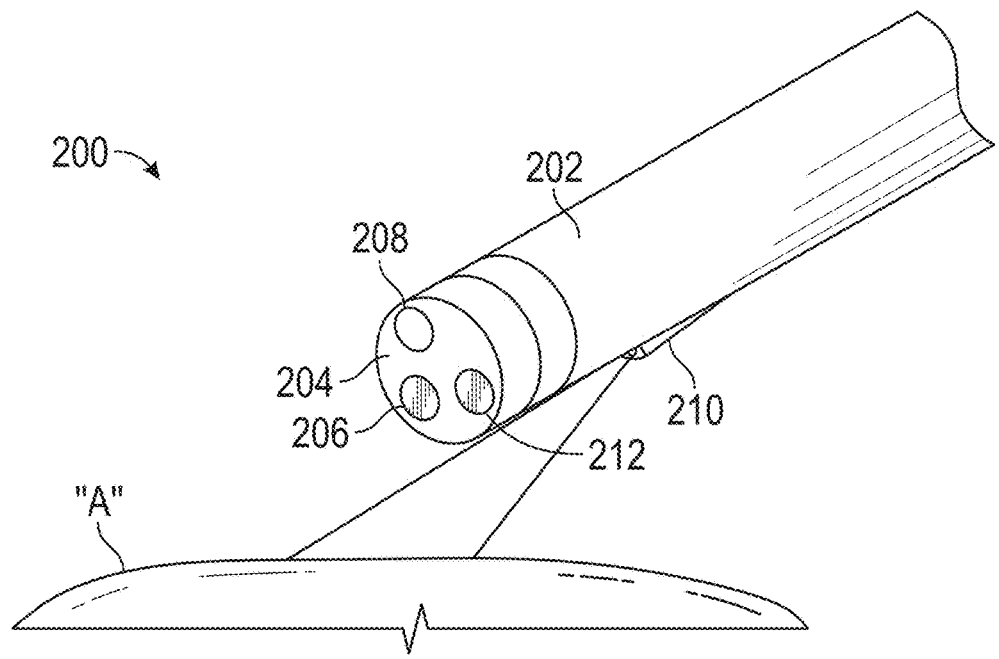
FIG. 3 is a front, perspective view, of a distal portion of the 3D endoscope of FIG. 1.

FIGS. 1-3 illustrate a system for enhanced surgical navigation in accordance with the disclosure which is generally described as system 100. System 100 includes a computing device 150 and a 3D endoscope 200 configured to scan a surgical site "S" of a patient "P". The 3D endoscope 200 is coupled to the computing device 150 and either the 3D endoscope 200 or the computing device is configured to generate a 3D spatial map of the surgical site "S".

The 3D endoscope 200 includes an elongate body 202 configured to be advanced within a suitable thoracic trocar (not shown) or other device capable of penetrating the chest cavity and receiving an endoscope therein or a thoracic catheter or the like. In embodiments, the elongate body 202 may include segments capable of being manipulated relative to one another. In this manner, the 3D endoscope 200 may be positioned in close proximity to the chest wall to navigate the shallow portions of the surgical site "S" (e.g., the thoracic cavity) between the lungs or other anatomy "A" (FIG. 1) and chest wall of the patient "P". As can be appreciated, the elongate body 202 may include any number of segments to aid in the maneuverability of the 3D endoscope 200 within the surgical site "S" (e.g., the thoracic cavity).

FIG. 2 illustrates the distal portion of the 3D endoscope 200, which includes an optical camera 206, a light source 208, a structured light projection source or structured light scanner (laser) 210, and a second camera 212. It is contemplated that each of the optical camera 206, light source 208, laser 210, and second camera 212 may be disposed or coupled to 3D endoscope 200 in any suitable configuration. The optical camera 206 is a visual-light optical camera, such as a charge-coupled device (CCD), complementary metal-oxide-semiconductor (CMOS), N-type metal-oxide-semiconductor (NMOS), or other suitable camera known in the art. In one non-limiting embodiment, the optical camera 206 is a CCD camera having a resolution of 1080p. The light source 208 is a light emitting diode (LED) emitting white light, although any light emitting device known in the art may be utilized. The laser 210 may be any structured light scanner known in the art, such as an LED or LED infrared laser that is dispersed into a scan pattern (line, mesh, or dots), by rotating mirror, beam splitter, diffraction grating, or panning of the laser 210 itself. In one non-limiting embodiment, the laser 210 is an LED laser having collimated light. The second camera 212 is a CCD camera capable of detecting IR light, although it is contemplated that the second camera 212 may detect visible light, such as visible green light or the like, depending upon the tissue being scanned. Specifically, visible green light contrasts with tissue having a red or pinkish hue enabling the second camera 212 to more easily identify the topography of the tissue. A digital filter (not shown) or a filter having narrow band optical grating (not shown) inhibits extraneous visible light emitted from the laser 210 from distracting the surgeon during the surgical procedure. In embodiments, the visible light is filtered from the image captured by the optical camera 206 and transmitted to the surgeon such that the image is clear and free from extraneous light patterns.

It is contemplated that the second camera 212 may be any thermographic camera known in the art, such as such as ferroelectric, silicon microbolometer, or uncooled focal plane array (UFPA), or may be any other suitable visible light camera such as a charge-coupled device (CCD), complementary metal-oxide-semiconductor (CMOS), N-type metal-oxide-semiconductor (NMOS), or other suitable camera known in the art where the light emitted from the laser 210 is in the visible or detectable spectrum. In embodiments, the distal surface 204 may include a suitable transparent protective cover (not shown) capable of inhibiting fluids or other contaminants from coming into contact with each of the optical camera 206, light source 208, laser 210, and second camera 212. Since the distance between the laser 210 and second camera 212 relative to the optical camera 206 is fixed (i.e., the offset of the optical camera 206 relative to the laser 210 and second camera 212), the images obtained by the optical camera 206 can more accurately be matched with a pre-operative image, as will be described in further detail hereinbelow.

In operation, initially, the patient "P" (FIG. 1) is imaged using any suitable imaging device (not shown), such as MRI, ultrasound, CT scan, Positron Emission Tomography (PET), or the like, and the images are stored within a memory (not shown) coupled to computing device 150. The memory may include any non-transitory computer-readable storage media for storing data and/or software that is executable by a processor (not shown) e.g., solid-state, volatile, non-volatile, removable, and non-removable.

After the patient "P" is imaged, the clinician penetrates the chest of a patient "P" using a trocar (not shown) or other suitable device. The distal portion of the 3D endoscope 200 is advanced within the trocar, and thereafter, within the surgical site "S" (e.g., the thoracic cavity) of the patient "P" (FIG. 2). As the 3D endoscope 200 is further advanced within the thoracic cavity, the clinician observes the images obtained by the optical camera on a display (not shown).

Once facing the surface of the anatomy "A", for example the lung "L" (e.g., incident the lung surface), the laser 210 emits IR light, which is reflected off the surface of the anatomy "A" and detected by the second camera 212. The 3D endoscope 200 is advanced over the surface of the anatomy "A" in a caudal, cephalad, or lateral direction, or combinations thereof. The data obtained by the second camera 212 is processed by the computing device 150 to generate a 3D spatial map of the surface of the surgical site "S" including the anatomy "A" and any objects present therein, such as surgical tools, using any suitable means, such as stitching or the like. In an aspect, the clinician advances the 3D endoscope 200 over the entire surface of the anatomy "A" in order to obtain as complete a map as possible.

The light source 208 and the optical camera 206 are simultaneously operated with the laser 210 and second camera 212 to permit correlation of the images received from the optical camera 206 with the previously acquired MRI (or other modality identified above) images. The correlation between the images obtained by the optical camera 206 and the previously acquired MRI images permits the clinician, and the computing device 150, to more accurately map the surface of the anatomy "A" and the surgical site "S". As can be appreciated, the accuracy of the correlation may be further improved using tracking software to track the distal tip of the 3D endoscope 200.

Referring now to FIGS. 4, 5A-5B, 6A-6B, 7, 8A-8B, 9, and 10A-10B, methods of enhanced surgical navigation using system 100 and various graphical user interfaces are illustrated and will be described. Although the methods illustrated and described herein are illustrated and described as being in a particular order and requiring particular steps, any of the methods may include some or all of the steps and may be implemented in any order. Additionally, any or all of the steps of any of the methods described herein may be carried out by computing device 150 of system 100 or any other component or combination of components of system 100, including the 3D endoscope 200. For example, in an aspect, the data captured by 3D endoscope 200 is transmitted to computing device 150 or another component for processing and generating of the 3D spatial map. Additionally, or alternatively, the data captured by 3D endoscope 200 may be processed by 3D endoscope 200 itself for generating of the 3D spatial map. To this end, some or all of the steps of any of the methods described herein may be carried out by some components while others are carried out by other components.

Figure 4:
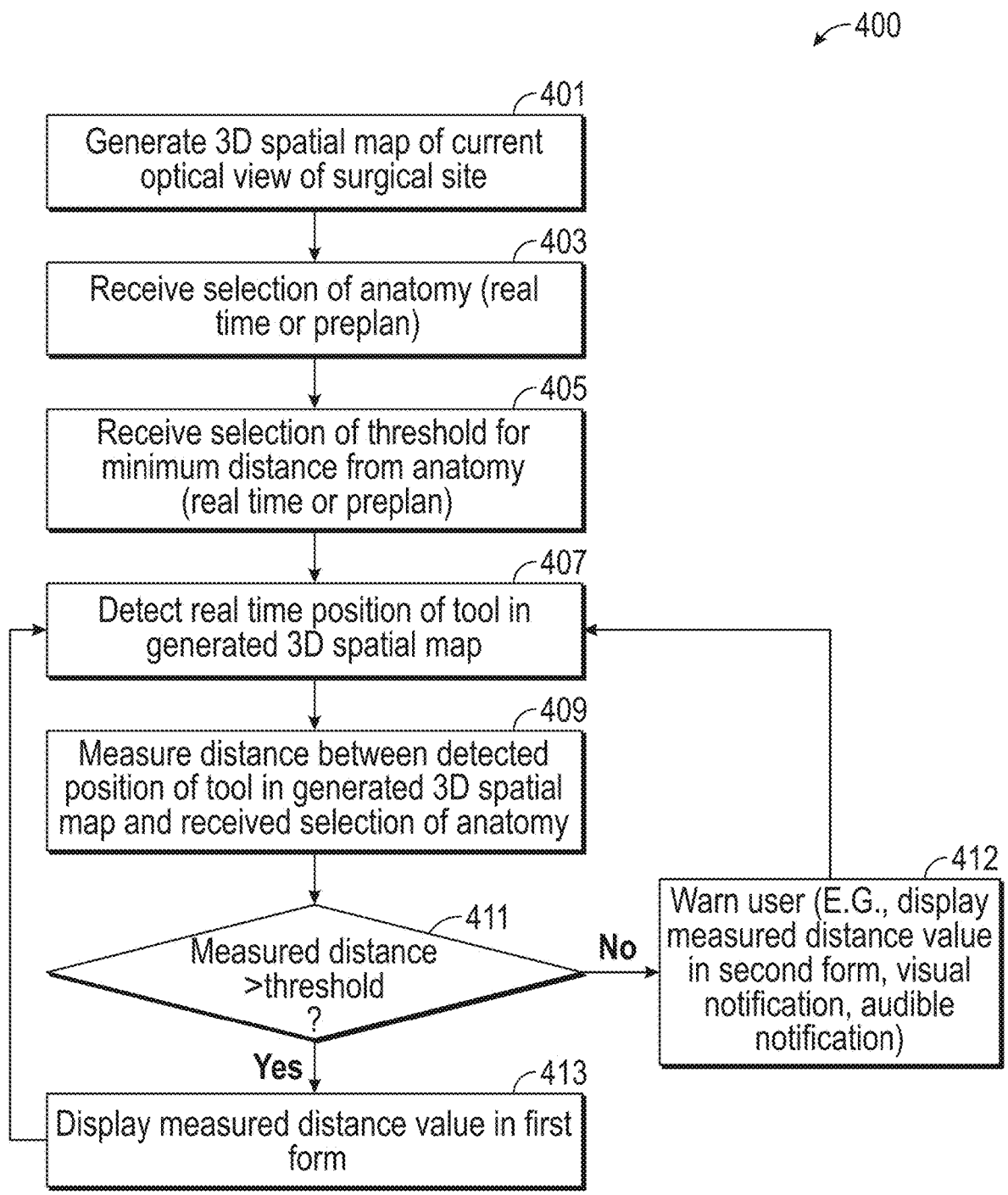
FIG. 4 is a flowchart illustrative of a method for measuring distances in a 3D spatial map and displaying values representing the measured distance in different forms in accordance with an aspect of the disclosure.
Figure 5A:
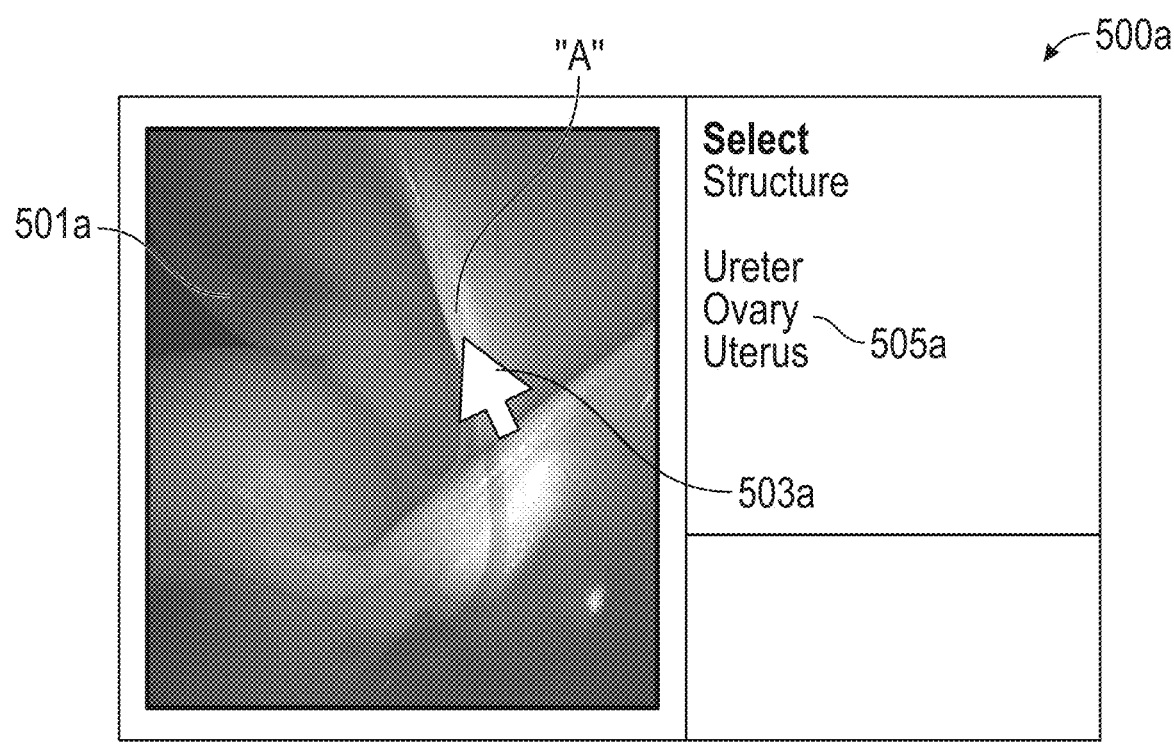
FIG. 5A is an exemplary graphical user interface for selecting an anatomical feature in accordance with an aspect of the disclosure.
Figure 5B:
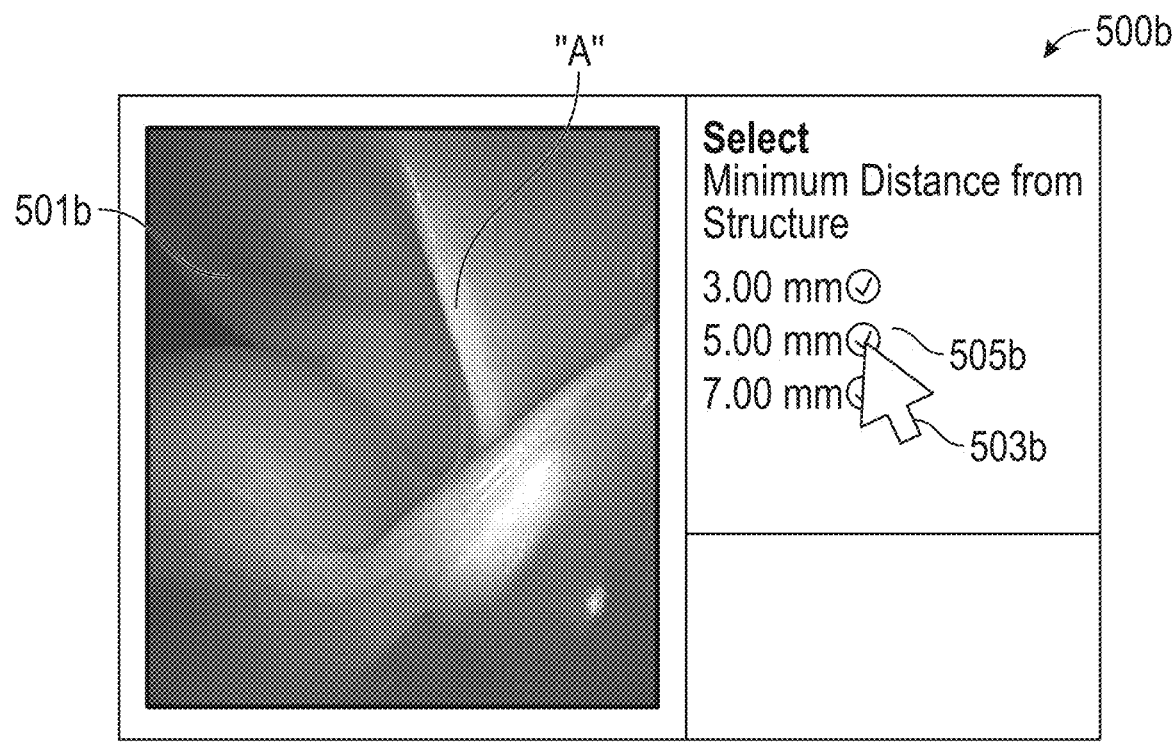
FIG. 5B is an exemplary graphical user interface for selecting a minimum distance threshold from a selected anatomical feature in accordance with an aspect of the disclosure.

FIG. 4 illustrates a flowchart of method 400, which is a method for enhanced surgical navigation which displays measured distances between a surgical tool "ST" (FIGS. 6A-6B) and a selected anatomy "A" and warns a user when the surgical tool "ST" is too close to the anatomy "A," for example, by displaying a value representing the distance measurement in multiple forms. Method 400 begins at step 401 where a 3D spatial map of a surgical site "S" is generated using a 3D endoscope 200 described above. A view of the surgical site "S", including the anatomy "A" within the surgical site and any surgical tools present therein, as captured by the 3D endoscope 200 is displayed in real time on a graphical user interface displayed on computing device 150.

In step 403, a selection of an anatomy "A" is made. This selection in step 403 may be carried out in real time using the images or data captured by the 3D endoscope 200 or during a planning phase using images or data captured by some other imaging device such as a fluoroscope, CT, MRI, or PET scanner. For example, referring briefly to FIG. 5A, the selection of the anatomy "A" of step 403 is shown using the graphical user interface 500a. Graphical user interface 500a includes a real time image 501a of the surgical site "S" as captured by 3D endoscope 200. A user may select the anatomy "A" in graphical user interface 500a via cursor 503a within the real time image 501a, via a selection of the name of the anatomy "A" from a list of anatomical features 505a detected within the real time image 501a, or via other means.

In step 405, a selection of a threshold minimum distance from the received selection of the anatomy "A" (selected in step 403) is made. The selection in step 405 may be carried out in real time using the images or data captured by the 3D endoscope 200 or during a planning phase using images, data captured by some other imaging device such as a fluoroscope, CT, MRI, or PET scanner, or preset preferences. For example, referring briefly to FIG. 5B, the selection of the threshold minimum distance from the received selection of the anatomy "A" of step 405 is shown using the graphical user interface 500b. Graphical user interface 500b includes a real time image 501b of the surgical site "S" as captured by 3D endoscope 200. A user may select the threshold minimum distance from the received selection of the anatomy "A" in graphical user interface 500b via cursor 503b within the real time image 501b or via a selection of distances from a list of preconfigured distances 505b. Additionally, or alternatively, the selection is a pre-set value based on user (e.g., surgeon) preference or defined by procedure type.

Once the anatomy "A" is selected (in step 403) and the threshold minimum distance is selected (step 405), method 400 proceeds to step 407 where a real time position of a surgical tool "ST" within the surgical site "S" in the 3D spatial map is determined.

In step 409, a distance between the detected position of the surgical tool "ST" in the generated 3D spatial map and the received selection of the anatomy "A" is measured by computing device 150. In an aspect, the 3D spatial map includes a matrix of equidistant data points representing fixed points in a current view of the surgical site "S" and a value of a data point represents an existence of an object at the data point in space. For example, one object can be any portion of the surgical tool "ST" and another object can be the anatomy "A" selected. The distance between the detected position of the surgical tool "ST" in the 3D spatial map and the received selection of the anatomy "A" in the 3D spatial map may be achieved by calculating a difference between coordinates of two data points (e.g., the point representing the surgical tool "ST" and the point representing the anatomy "A") in the matrix. In an aspect, the surgical tool "ST" and the anatomy "A" can be represented by a line of points where the distance can be the smallest distance between any point of the surgical tool "ST" and any point of the anatomy "A."

Additionally, or alternatively, the distance between the detected position of the surgical tool "ST" in the 3D spatial map and the received selection of the anatomy "A" in the 3D spatial map may be achieved by following a contour of a surface between two data points (e.g., the point representing the surgical tool "ST" and the point representing the anatomy "A") in the matrix and calculating a distance along the contour. In an aspect, two contours are considered where two points on the anatomy "A" and two points on the surgical tool "ST" are factors, and where the method 400 further includes determining the distance between the two contours and/or determining the distance between each contour and the surgical tool "ST."

Figure 6A:
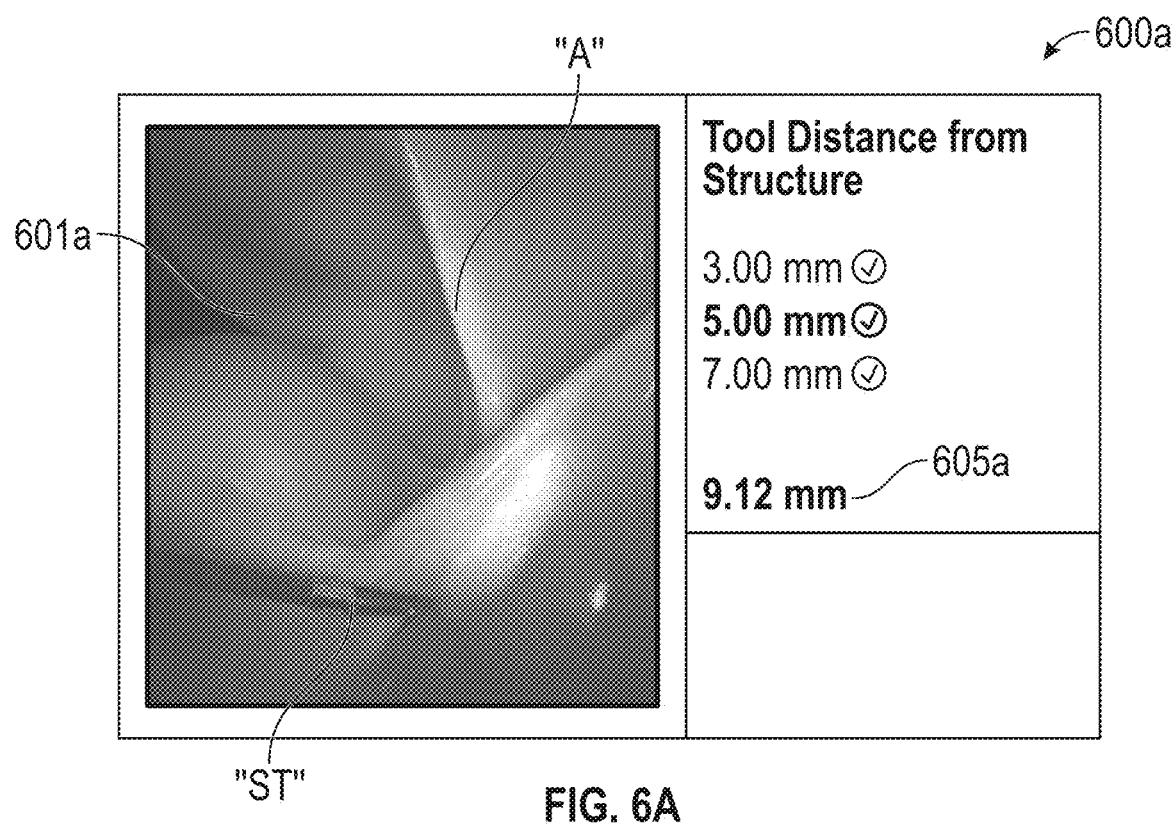
FIG. 6A is an exemplary graphical user interface displaying numerical values representing a distance between a surgical tool and an anatomical feature in a first form when the surgical tool is a first distance from the anatomical feature in accordance with the method of FIG. 4.
Figure 6B:
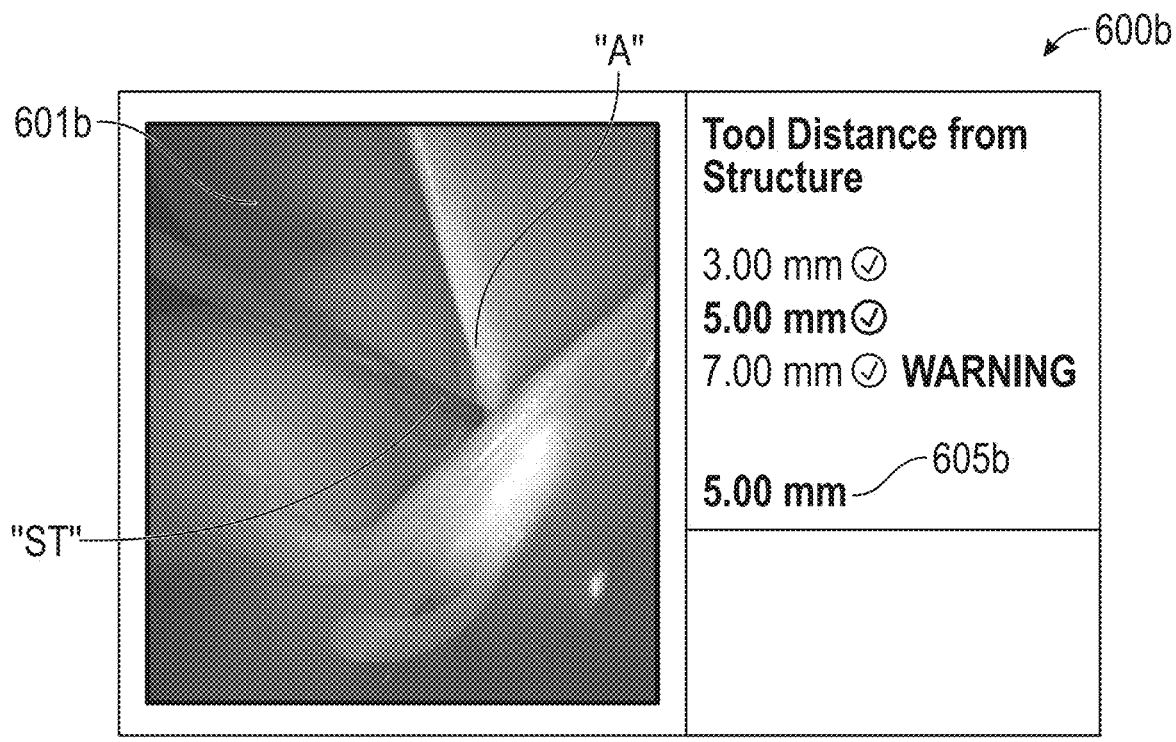
FIG. 6B is an exemplary graphical user interface displaying numerical values representing a distance between a surgical tool and an anatomical feature in a second form when the surgical tool is a second distance from the anatomical feature in accordance with the method of FIG. 4.

Following the measurement in step 409, in step 411, a determination is made as to whether or not the measured distance (from step 409) is greater than the threshold selected in step 405. If the measured distance is greater than the selected threshold (yes in step 411), then method 400 proceeds to step 413, where the value of the measured distance is displayed in a first (normal) form 605a (FIG. 6A). Such a display is illustrated in the graphical user interface 600a shown in FIG. 6A, which includes a real time image 601a of the surgical site "S", the current real time position of the surgical tool "ST", the selected anatomy "A", and the value of the measured distance in a first form 605a. This displayed value is updated in real time as the surgical tool "ST" is moved about within the surgical site "S" and/or as the anatomy "A" moves within the surgical site "S" (for example, due to breathing or other factors).

On the other hand, if the measured distance is equal to or not greater than the selected threshold (no in step 411), then method 400 proceeds to step 412 where the user is warned that the surgical tool "ST" is currently too close to the anatomy "A". This warning may be in the form of displaying the value of the measured distance in a second form 605b (FIG. 6B), different from the first (normal) form of the displayed value, for example via a larger text, different color text, and/or flashing text, via a displayed warning message, via an audible warning, via a tactile feedback warning having a specific signature, or any combination thereof. For example, such a display is illustrated in the graphical user interface 600b shown in FIG. 6B, which includes a real time image 601b of the surgical site "S", the current real time position of the surgical tool "ST", the selected anatomy "A", and the value of the measured distance in a second form 605b. In robotic applications, the warning may be in the form of preventing motion (e.g., motion of a surgical tool or a portion thereof) that would violate the distance (e.g., threshold).

Figure 7:
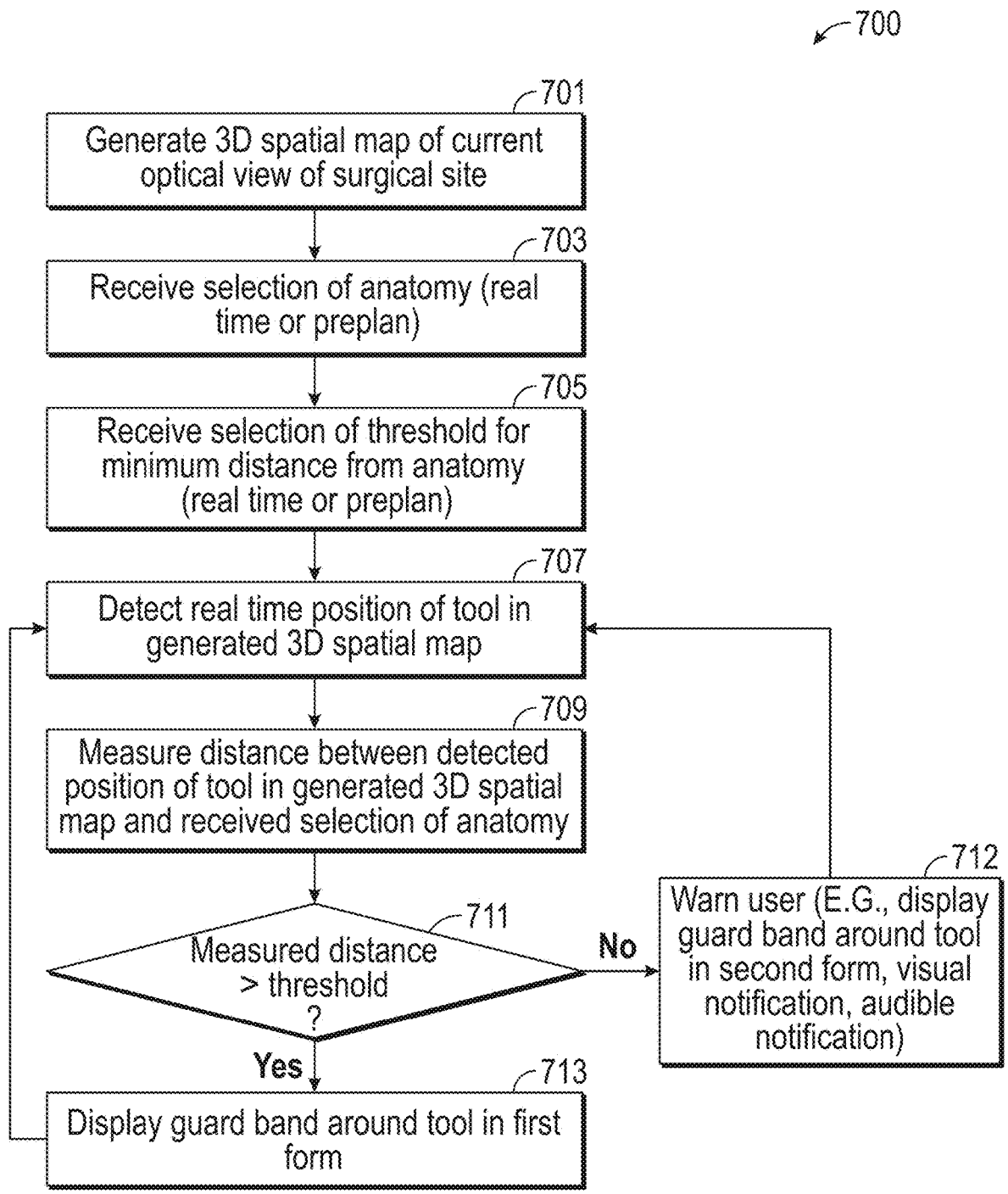
FIG. 7 is a flowchart illustrative of a method for measuring distances in a 3D spatial map and displaying guard bands around a surgical tool in accordance with the disclosure.
Figure 8A:
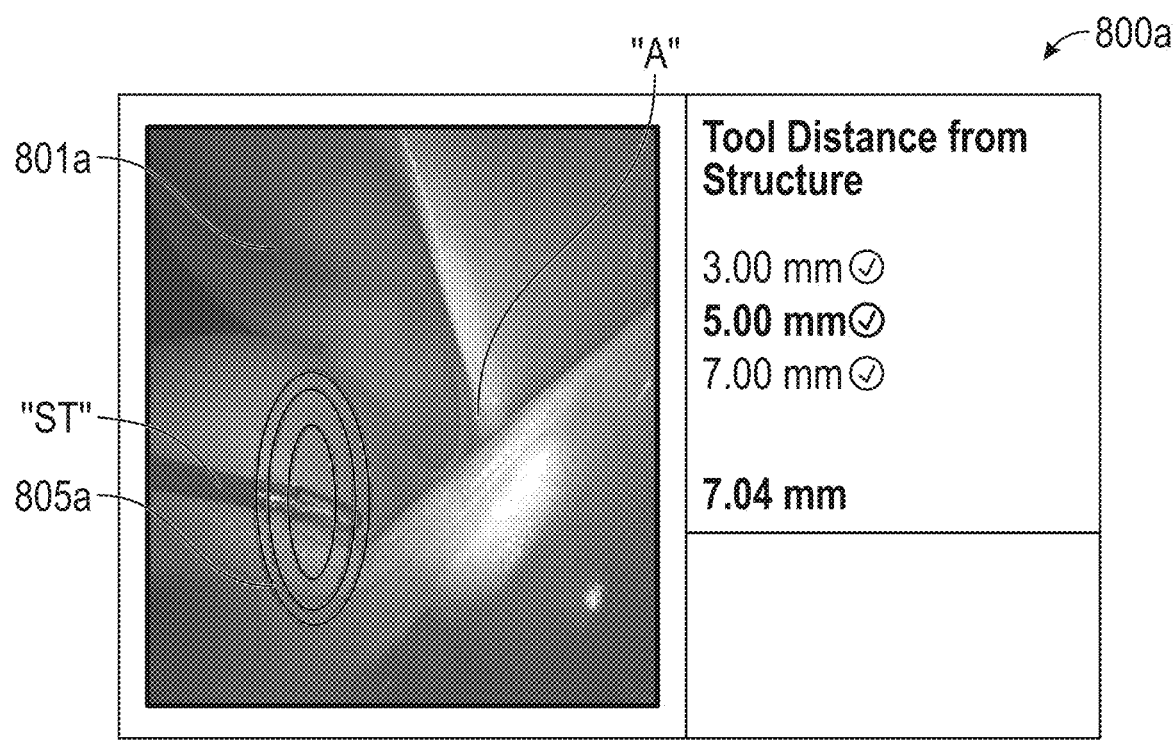
FIG. 8A is an exemplary graphical user interface displaying guard bands around a surgical tool when the surgical tool is a first distance from an anatomical feature in accordance with the method of FIG. 7.
Figure 8B:
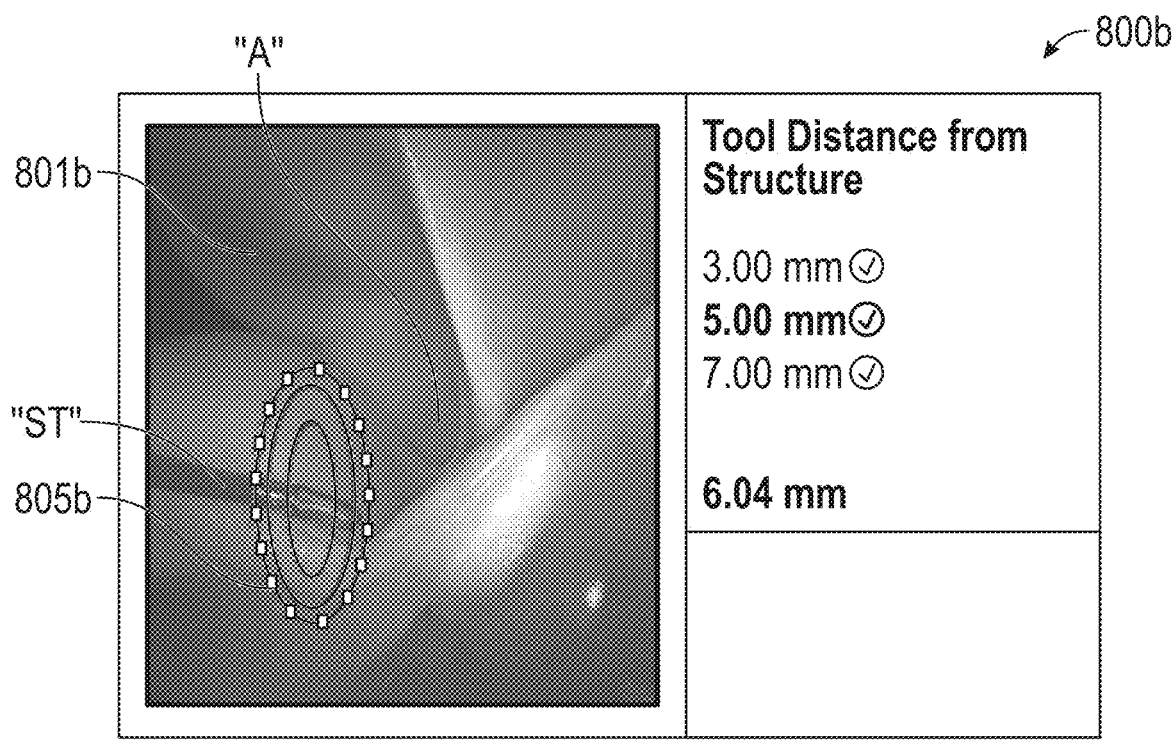
FIG. 8B is an exemplary graphical user interface displaying guard bands around a surgical tool when the surgical tool is a second distance from an anatomical feature in accordance with the method of FIG. 7.

FIG. 7 illustrates a flowchart of method 700, which is a method for enhanced surgical navigation which displays at least one guard band (FIGS. 8A-8B) around a surgical tool "ST" (FIGS. 8A-8B) and warns a user when the surgical tool "ST" is too close to the anatomy "A". Steps 701, 703, 705, 707, 709, and 711 of method 700 are identical to steps 401, 403, 405, 407, 409, and 411 of method 400, respectively, and therefore will not be described for brevity.

In step 711, if the measured distance is greater than the selected threshold (yes in step 711), then method 700 proceeds to step 713, where at least one guard band 805a (FIG. 8A) is displayed in a first form around a distal portion of the surgical tool "ST". When a plurality of guard bands is displayed, each guard band may be evenly spaced relative to the other based on a preconfigured distance. Such a display is illustrated in the graphical user interface 800a shown in FIG. 8A, which includes a real time image 801a of the surgical site "S", the current real time position of the surgical tool "ST", the selected anatomy "A", and a plurality of guard bands 805a in a first form around a distal portion of the surgical tool "ST". The displayed guard bands 805a is updated in real time as the surgical tool "ST" is moved about within the surgical site "S" and/or as the anatomy "A" moves within the surgical site "S" (for example, due to breathing or other factors).

On the other hand, if the measured distance is equal to or not greater than the selected threshold (no in step 711), then method 700 proceeds to step 712 where the user is warned that the surgical tool "ST" is currently too close to the anatomy "A". This warning may be in the form of displaying at least one of the guard bands 805a (FIG. 8A) in a second form 805b (FIG. 8B), different from the first (normal) form of the displayed guard hand 805a, for example via a thicker hand, different color band, broken-lined band, and/or flashing band, via a displayed warning message, via an audible warning, via a tactile feedback warning having a specific signature, or any combination thereof. For example, such a display is illustrated in the graphical user interface 800b shown in FIG. 8B, which includes a real time image 801b of the surgical site "S", the current real time position of the surgical tool "ST", the selected anatomy "A", and the outermost guard band 805b in a second form (e.g., as a broken-lined band).

Figure 9:
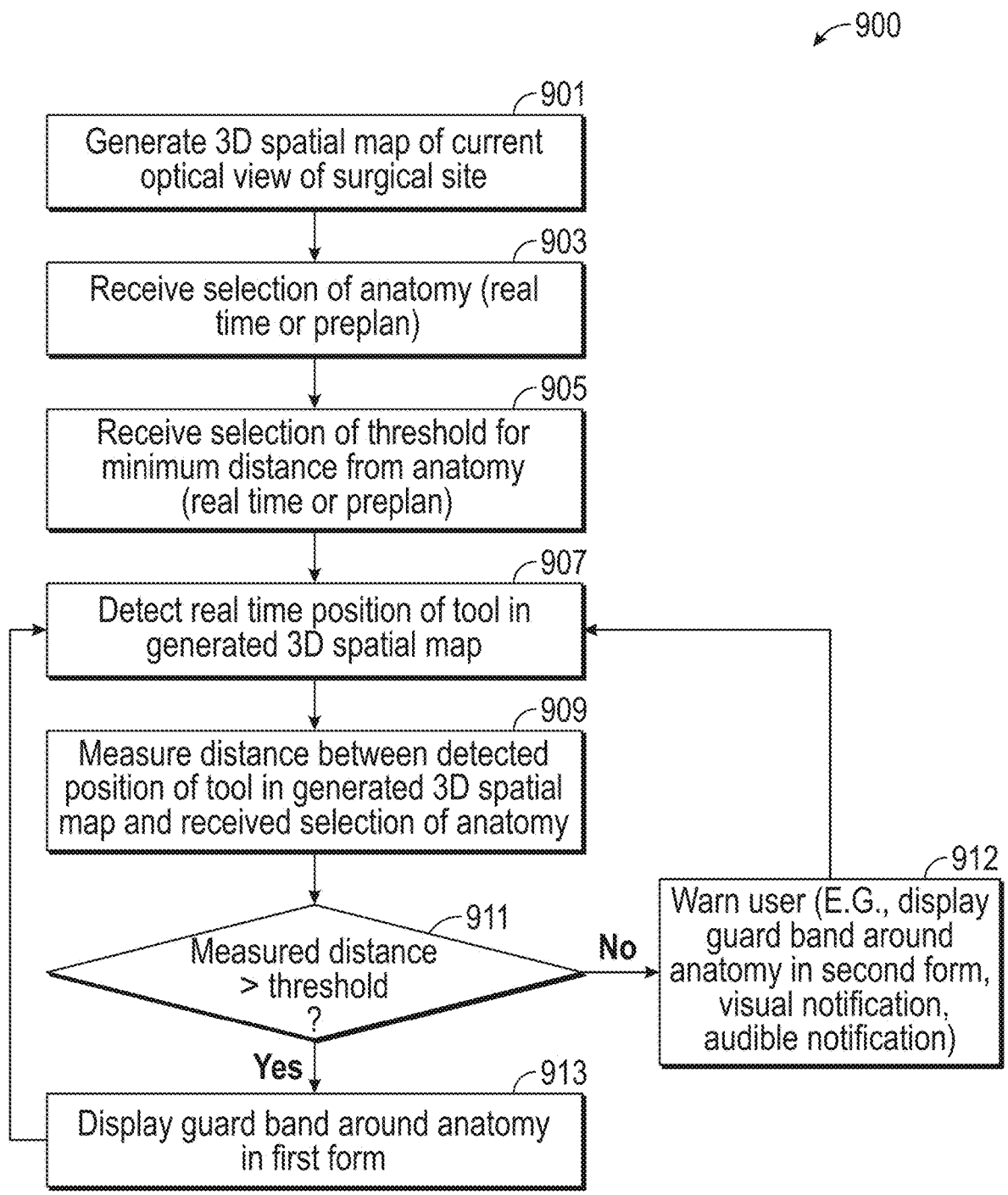
FIG. 9 is a flowchart illustrative of a method for measuring distances in a 3D spatial map and displaying guard bands around an anatomical feature in accordance with the disclosure.
Figure 10A:
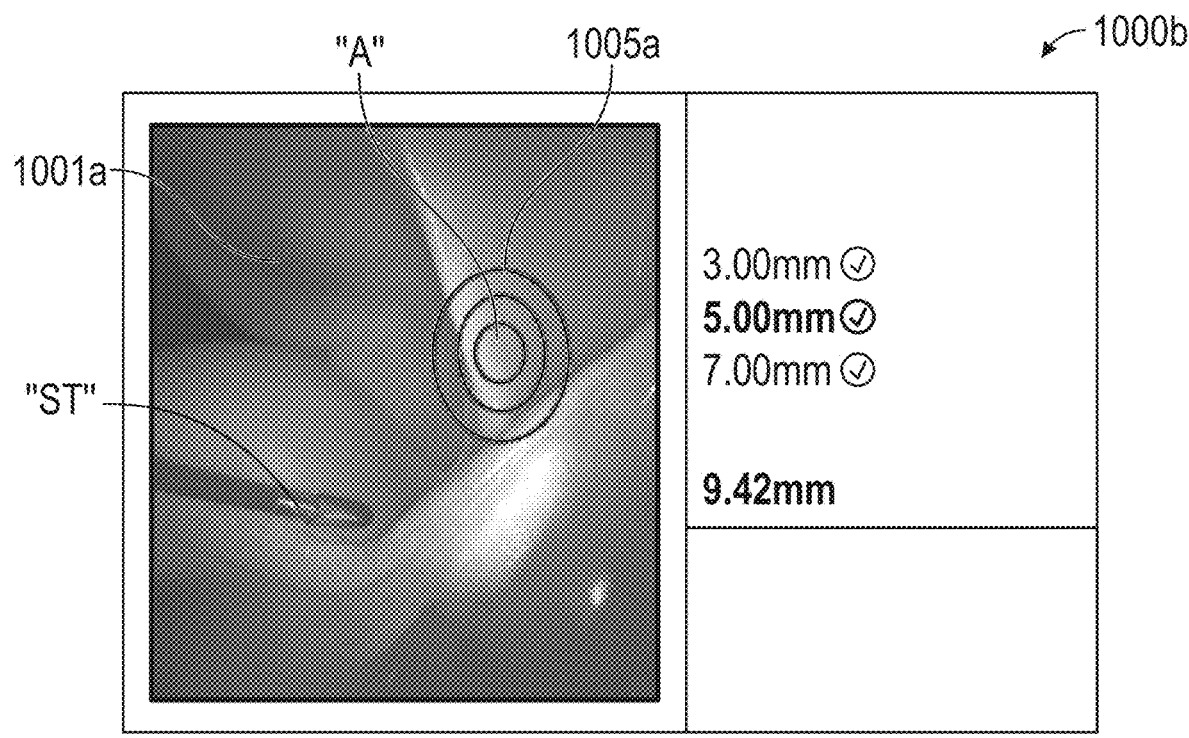
FIG. 10A is an exemplary graphical user interface displaying guard bands around an anatomical feature when a surgical tool is a first distance from the anatomical feature in accordance with the method of FIG. 9.
Figure 10B:
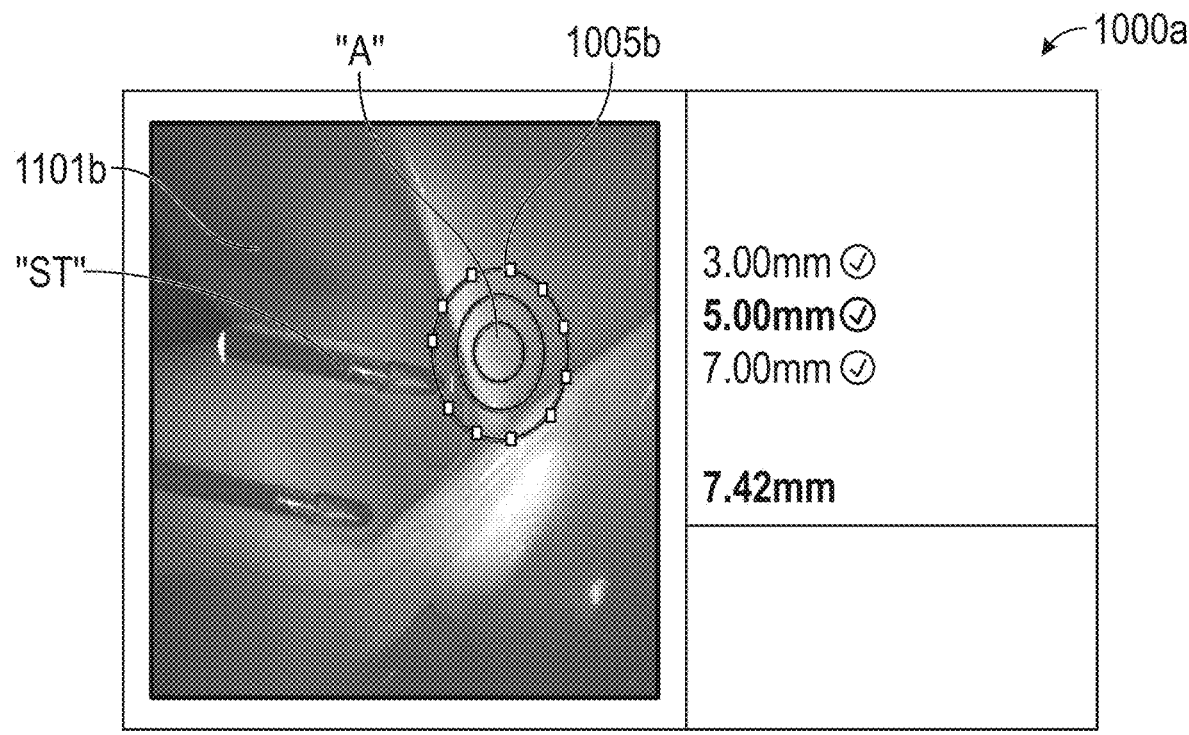
FIG. 10B is an exemplary graphical user interface displaying guard bands around an anatomical feature when a surgical tool is a second distance from the anatomical feature in accordance with the method of FIG. 9.

FIG. 9 illustrates a flowchart of method 900, which is a method for enhanced surgical navigation which displays at least one guard band (FIGS. 10A-10B) around an anatomy "A" (FIGS. 10A-10B) and warns a user when the surgical tool "ST" is too close to the anatomy "A". Steps 901, 903, 905, 907, 909, and 911 of method 900 are identical to steps 401, 403, 405, 407, 409, and 411 of method 400, respectively, and therefore will not be described for brevity.

In step 911, if the measured distance is greater than the selected threshold (yes in step 911), then method 900 proceeds to step 913, where at least one guard band 1005a (FIG. 10A) is displayed in a first form around the anatomy "A". When a plurality of guard bands is displayed, each guard band may be evenly spaced relative to the other based on a preconfigured distance. Such a display is illustrated in the graphical user interface 1000a shown in FIG. 10A, which includes a real time image 1001a of the surgical site "S", the current real time position of the surgical tool "ST", the selected anatomy "A", and a plurality of guard bands 1005a in a first form around the selected anatomy "A". The displayed guard hands 1005a is updated in real time as the surgical tool "ST" is moved about within the surgical site "S" and/or as the anatomy "A" moves within the surgical site "S" (for example, due to breathing or other factors).

On the other hand, if the measured distance is equal to or not greater than the selected threshold (no in step 911), then method 900 proceeds to step 912 where the user is warned that the surgical tool "ST" is currently too close to the anatomy "A". This warning may be in the form of displaying at least one of the guard bands 1005a (FIG. 10A) in a second form 1005b (FIG. 10B), different from the first (normal) form of the displayed guard band 1005a, for example via a thicker hand, different color band, broken-lined band, and/or flashing band, via a displayed warning message, via an audible warning, via a tactile feedback warning having a specific signature, or any combination thereof. For example, such a display is illustrated in the graphical user interface 1000b shown in FIG. 10B, which includes a real time image 1001b of the surgical site "S", the current real time position of the surgical tool "ST", the selected anatomy "A", and the outermost guard band 1005b in a second form (e.g., as a broken-lined band).

Figure 12:
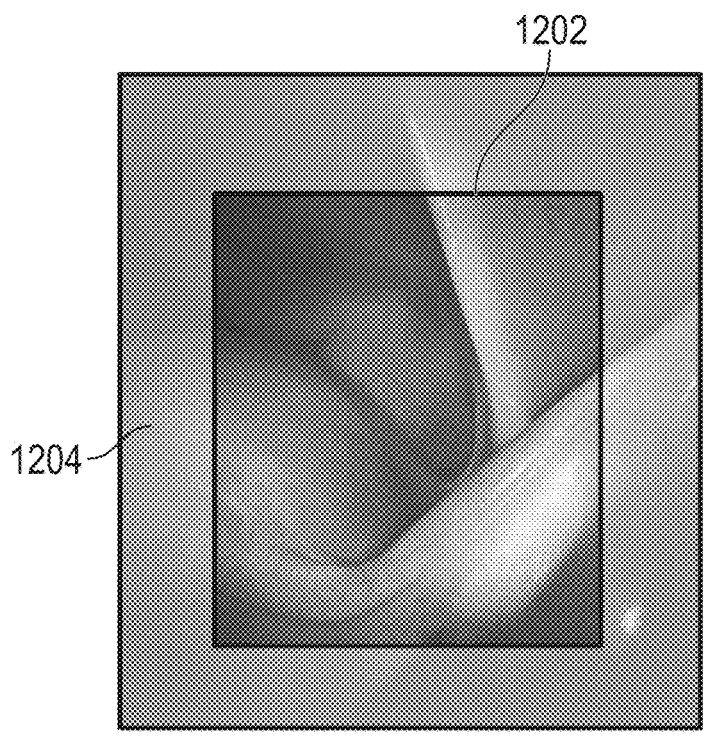
FIG. 12 is an exemplary graphical user interface displaying items within a current field of view and items outside a current field of view.

In addition to the above-described methods performable by system 100, system 100 may detect coordinate mismatches and notify the user or modify the display of the graphical user interface based on the detected mismatch. The anatomy being scanned is not static and will change over time due to elements such as manipulation by the surgeon, natural biological rhythms (e.g. cardiac, pulmonary), and gravity. Detection of such changes by system 100 can include 3D coordinate mismatches between current scanned locations of objects in the current field of view and those from a previous view (e.g., a surface that extends out of the current view where the Y coordinates of the surface in view differs from that outside). Previously scanned structures completely outside of the current view may change as well. In an aspect, system 100 indicates to the user that all items outside the current field of view may have changed. To this end, system 100 may modify the displayed image of all elements outside the current field of view via blurring, removing 3D effects (e.g., flattening the image), and removal of color or fading of color. Additionally, or alternatively, the items within the field of view may continue to be updated in real-time by system 100. FIG. 12 is an exemplary user interface of system 100, zoomed out, which includes items within the current field of view 1202, displayed normally and updated in real-time (e.g., in three-dimension), and items outside the current field of view 1204, displayed abnormally (e.g., flat with no 3D aspects). Each technique can have subtleties such as keying the extent of the effect to the age of the image since it was last refreshed.

Surgical instruments such as the endoscopes, computing devices, and other components of system 100 described herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, endoscopes, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

It is contemplated that the endoscopes described herein may be positioned by the robotic system and the precise position of the endoscope transmitted to the computer to construct the 3D image of the scanned organ or operative field. The robotic system has the ability to autonomously scan the surgical field and construct a complete 3D model of the field to aid the surgeon in directing the robotic arms or to provide necessary 3D information for the robotic system to further conduct surgical steps autonomously. In embodiments, where the endoscope includes a camera and a structured light source that are independent of one another, the robotic system may direct the camera and a structured light source separately. The robotic system provides the relative coordinates between respective endoscopes needed to triangulate the points in the structured light and camera views to construct a 3D surface of the operative field. In this manner, the robotic system has a specific advantage of being able to autonomously position the structure light source onto the field of view of the camera or camera endoscope. Additionally, or alternatively, with the robot controlling the camera location (or other component location), the robot may move the camera (or other component) to expand the size of the scanned anatomy (e.g., the amount scanned) to create a larger view for the user (e.g., surgeon) without input or knowledge by the user.

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Figure 11:
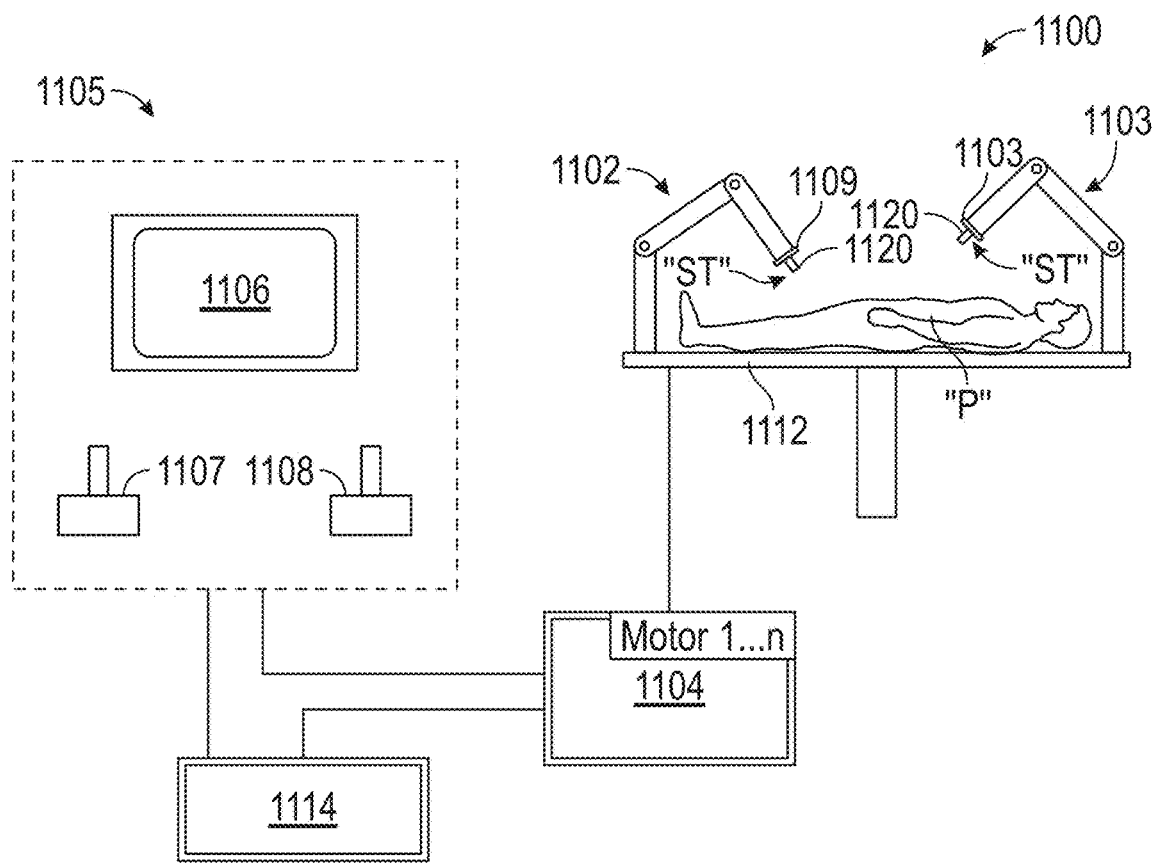
FIG. 11 is a schematic illustration of a robotic surgical system configured for use in accordance with the disclosure.

Referring to FIG. 11, a medical workstation is shown generally as workstation 1100 and generally may include a plurality of robot arms 1102, 1103, a control device 1104, and an operating console 1105 coupled with control device 1104. Operating console 1105 may include a display device 1106, which may be set up in particular to display 3D images, and manual input devices 1107, 1108, by means of which a person (not shown), for example a surgeon, may be able to telemanipulate robot arms 1102, 1103 in a first operating mode.

Each of the robot arms 1102, 1103 may include a plurality of members, which are connected through joints, and an attaching device 1109, 1111, to which may be attached, for example, a surgical tool "ST" supporting an end effector 1120, in accordance with any one of several embodiments disclosed herein, as will be described in greater detail below.

Robot arms 1102, 1103 may be driven by electric drives (not shown) that are connected to control device 1104. Control device 1104 (e.g., a computer) may be set up to activate the drives, in particular by means of a computer program, in such a way that robot arms 1102, 1103, their attaching devices 1109, 1111 and thus the surgical tool (including end effector 1120) execute a desired movement according to a movement defined by means of manual input devices 1107, 1108. Control device 1104 may also be set up in such a way that it regulates the movement of robot arms 1102, 1103 and/or of the drives.

Medical workstation 1100 may be configured for use on a patient "P" lying on a patient table 1112 to be treated in a minimally invasive manner by means of end effector 1120. Medical workstation 1100 may also include more than two robot arms 1102, 1103, the additional robot arms likewise being connected to control device 1104 and being telemanipulatable by means of operating console 1105. A medical instrument or surgical tool (including an end effector 1120) may also be attached to the additional robot arm, Medical workstation 1100 may include a database 1114, in particular coupled to with control device 1104, in which are stored, for example, pre-operative data from patient/living being "P" and/or anatomical atlases.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments.

As used hereinabove, the term "clinician" refers to a doctor, a nurse, or any other care provider and may include support personnel. Throughout this description, the term "proximal" refers to the portion of the device or component thereof that is closer to the clinician and the term "distal" refers to the portion of the device or component thereof that is farther from the clinician. Additionally, in the drawings and in the description above, terms such as front, rear, upper, lower, top, bottom, and similar directional terms are used simply for convenience of description and are not intended to limit the disclosure. In the description hereinabove, well-known functions or constructions are not described in detail to avoid Obscuring the disclosure in unnecessary detail.

What is claimed is:

1. A method for enhanced surgical navigation comprising:
generating a 3D spatial map of a surgical site using a 3D endoscope, the 3D endoscope including a light emitting diode (LED), a camera configured to capture reflected light from the LED, and a structured light source;
detecting a position of a surgical tool in the generated 3D spatial map;

detecting a location of an anatomy in the generated 3D spatial map;

measuring a distance between the detected position of the surgical tool in the generated 3D spatial map and the location of the anatomy in the 3D spatial map;

determining whether the measured distance between the detected position of the surgical tool in the generated 3D spatial map and the location of the anatomy in the generated 3D spatial map is greater than a threshold minimum distance;

displaying a first band in a first form on the 3D spatial map and in a user interface, the first band having an outer dimension corresponding to the threshold minimum distance, the first band being displayed around the surgical tool or the anatomy;

displaying a second band on the 3D spatial map and in the user interface, wherein the second band is displayed around the surgical tool or the anatomy and includes an outer dimension that is different from the outer dimension of the first band; and generating a warning when it is determined that the measured distance between the detected position of the surgical tool in the generated 3D spatial map and the location of the anatomy in the generated 3D spatial map is equal to or not greater than the threshold minimum distance from the location of the anatomy in the generated 3D spatial map, wherein the warning is displaying the first band in a second form on the 3D spatial map of the surgical site and in the user interface, the displayed second form of the first band having an outer dimension equal to the outer dimension of the displayed first form of the first band, the second form of the first band being displayed around the surgical tool or the anatomy, wherein the outer dimension of the displayed second band does not change.

2. The method of claim 1, further comprising:

displaying a value in the user interface representing the measured distance between the detected position of the surgical tool in the generated 3D spatial map and the location of the anatomy in the generated 3D spatial map in a first form when it is determined that the measured distance between the detected position of the surgical tool in the generated 3D spatial map and the location of the anatomy in the generated 3D spatial map is greater than the threshold minimum distance from the location of the anatomy in the generated 3D spatial map, and wherein generating the warning includes displaying the value in a second form different from the first form.

3. The method of claim 1, further comprising detecting the location of the anatomy in the generated 3D spatial map of the surgical site by receiving a selection from pre-surgical imagery during a planning phase, the pre-surgical imagery including at least one of CT, MRI, fluoroscopic, ultrasound, or any combinations thereof.

4. The method of claim 1, further comprising detecting the location of the anatomy in the generated 3D spatial map of the surgical site by receiving a selection from surgical imagery during a surgical phase from images generated from the 3D endoscope.

5. The method of claim 1, further comprising receiving a selection of the threshold minimum distance from the location of the anatomy in the generated 3D spatial map by receiving the selection from pre-surgical imagery during a planning phase, the pre-surgical imagery including at least one of CT, MRI, fluoroscopic, ultrasound, or any combinations thereof.

6. The method of claim 1, further comprising receiving a selection of the threshold minimum distance from the location of the anatomy in the generated 3D spatial map by receiving the selection from surgical imagery during a surgical phase from images generated from the 3D endoscope.

7. The method of claim 1, wherein the 3D spatial map includes a matrix of equidistant data points representing fixed points in a current view of the surgical site and a value of a data point represents an existence of an object at the data point in space.

8. The method of claim 7, wherein measuring the distance between the detected position of the surgical tool in the generated 3D spatial map and the location of the anatomy in the generated 3D spatial map includes at least one of:

calculating a difference between coordinates of two data points in the matrix; or following a contour of a surface between two data points in the matrix and calculating a distance along the contour.

9. The method of claim 1, wherein one or both of the first and second bands may change form.

10. A system for enhanced surgical navigation comprising:

a 3D endoscope including a light emitting diode (LED), a camera configured to capture reflected light from the LED, and a structured light source, wherein the camera and the structured light source are configured to generate a 3D spatial map of a surgical site; and a computing device operably coupled to the 3D endoscope and configured to:

display the 3D spatial map of the surgical site on a graphical user interface, wherein the 3D spatial map includes a matrix of equidistant data points representing fixed points in a current view of the surgical site and a value of a data point represents an existence of an object at the data point in space;

detect a position of a surgical tool in the generated 3D spatial map;

measure a distance between the detected position of the surgical tool in the generated 3D spatial map and a location of an anatomy in the generated 3D spatial map;

determine whether the measured distance between the detected position of the surgical tool in the generated 3D spatial map and the location of the anatomy in the generated 3D spatial map is greater than a threshold minimum distance from the location of the anatomy in the generated 3D spatial map;

display a first band in a first form on the 3D spatial map and in the graphical user interface, the first band having an outer dimension corresponding to the threshold minimum distance, the first band being displayed around the surgical tool or the anatomy;

display a second band on the 3D spatial map and in the user interface, wherein the second band is displayed around the surgical tool or anatomy and includes an outer dimension that is different from the outer dimension of the first band; and generate a warning when it is determined that the measured distance between the detected position of the surgical tool in the generated 3D spatial map and the location of the anatomy in the generated 3D spatial map is equal to or not greater than the threshold minimum distance from the location of the anatomy in the generated 3D spatial map, wherein the warning is displaying the first band in a second form on the 3D spatial map of the surgical site and in the graphical user interface, the displayed second form of the first band having an outer dimension equal to the outer dimension of the displayed first form of the first band, the second form of the first band being displayed around the surgical tool or the anatomy, wherein the outer dimension of the displayed second band does not change.

11. The system of claim 10, wherein the computing device is further configured to:
  display, on the graphical user interface, a value representing the measured distance between the detected position of the surgical tool in the generated 3D spatial map and the location of the anatomy in the generated 3D spatial map in a first form when it is determined that the measured distance between the detected position of the surgical tool in the generated 3D spatial map and the location of the anatomy in the generated 3D spatial map is greater than the threshold minimum distance from the location of the anatomy in the generated 3D spatial map; and
  display, on the graphical user interface, the value in a second form different form the first form when it is determined that the measured distance between the detected position of the surgical tool in the generated 3D spatial map and the location of the anatomy in the generated 3D spatial map is equal to or not greater than the threshold minimum distance from the location of the anatomy in the generated 3D spatial map.

12. The system of claim 10, wherein the computing device detects the location of the anatomy in the generated 3D spatial map of the surgical site by receiving a selection from pre-surgical imagery during a planning phase, the pre-surgical imagery including at least one of CT, MRI, fluoroscopic, ultrasound, or any combinations thereof.

13. The system of claim 10, wherein the computing device detects the location of the anatomy in the generated 3D spatial map of the surgical site by receiving a selection from surgical imagery during a surgical phase from images generated from the 3D endoscope.

14. The system of claim 10, wherein the computing device receives a selection of the threshold minimum distance from the location of the anatomy in the generated 3D spatial map by receiving the selection from pre-surgical imagery during the planning phase, the pre-surgical imagery including at least one of CT, MRI, fluoroscopy, ultrasound, or any combinations thereof.

15. The system of claim 10, wherein the computing device receives a selection of the threshold minimum distance from the location of the anatomy in the generated 3D spatial map be receiving the selection from surgical imagery during a surgical phase from images generated from the 3D endoscope.

16. The system of claim 10, wherein the computing device measures the distance between the detected position of the surgical tool in the generated 3D spatial map and the location of the anatomy in the generated 3D spatial map by calculating a difference between coordinates of two data points in the matrix.

17. The system of claim 16, wherein the computing device measures the distance between the detected position of the surgical tool in the generated 3D spatial map and the location of the anatomy in the generated 3D spatial map by following a contour of a surface between two data points in the matrix and calculating a distance along the contour.

18. The system of claim 10, wherein one or both of the first and second bands may change form.

19. A non-transitory computer-readable storage medium encoded with a program that, when executed by a processor, causes the processor to:
  generate a 3D spatial map of a surgical site from light emitted by a light emitting diode (LED) reflected from the surgical site and captured by a camera,
  detect a position of a surgical tool in the generated 3D spatial map based on captured reflections from a structured light source;
  determine whether a distance between the detected position of the surgical tool in the generated 3D spatial map and a location of an anatomy in the 3D spatial map is greater than a threshold minimum distance;
  display a first band in a first form on the 3D spatial map and in a user interface, the first band having an outer dimension corresponding to the threshold minimum distance, the first band being displayed around the surgical tool or the anatomy;
  display a second band on the 3D spatial map and in the user interface, wherein the second band is displayed around the surgical tool or anatomy and includes an outer dimension that is different from the outer dimension of the first band; and
  generate a warning when it is determined that the distance between the detected position of the surgical tool in the generated 3D spatial map and the location of the anatomy in the generated 3D spatial map is equal to or not greater than the threshold minimum distance, wherein the warning is displaying the first band in a second form on the 3D spatial map of the surgical site and in the user interface, the displayed second form of the first band having an outer dimension equal to the outer dimension of the displayed first form of the first band, the second form of the first band being displayed around the surgical tool or the anatomy, wherein the outer dimension of the displayed second band does not change.

20. The non-transitory computer-readable storage medium of claim 19, wherein one or both of the first and second bands may change form,
  wherein the 3D spatial map includes a matrix of equidistant data points representing fixed points in a current view of the surgical site and a value of a data point represents an existence of an object at the data point in space, and the distance between the detected position of the surgical tool in the generated 3D spatial map and the location of the anatomy in the generated 3D spatial map is measured based on at least one of:
    calculating a difference between coordinates of two data points in the matrix; or
    following a contour of a surface between two data points in the matrix and calculating a distance along the contour.

* * * * *